US005856437A

United States Patent [19]
Miyamura et al.

[11] Patent Number: 5,856,437
[45] Date of Patent: Jan. 5, 1999

[54] HEPATITIS C VIRUS ISOLATE POLYPEPTIDES

[75] Inventors: Tatsuo Miyamura; Izumi Saito, both of Tokyo, Japan; Michael Houghton, Danville, Calif.; Amy J. Weiner, Benicia, Calif.; Jang Han, Lafayette, Calif.; Janice A. Kolberg, Hercules, Calif.; Tai-An Cha, San Ramon, Calif.; Bruce D. Irvine, Concord, Calif.

[73] Assignees: Chiron Corporation, Emeryville, Calif.; The Director General of the National Institute of Health of Japan, Tokyo, Japan

[21] Appl. No.: 334,255

[22] Filed: Nov. 3, 1994

Related U.S. Application Data

[62] Division of Ser. No. 201,066, Feb. 24, 1994, Pat. No. 5,372,928, which is a continuation of Ser. No. 101,280, Aug. 2, 1993, which is a continuation of Ser. No. 637,380, Jan. 4, 1991, which is a continuation-in-part of Ser. No. 456,142, Dec. 21, 1989, abandoned, which is a continuation-in-part of Ser. No. 408,045, Sep. 15, 1989, abandoned.

[51] Int. Cl.$^6$ .......................... A61K 38/04; A61K 39/12; A61K 39/29; C12Q 1/70
[52] U.S. Cl. .......................... 530/350; 435/5; 435/235.1; 530/300; 530/324; 530/325; 530/326; 530/327; 530/328; 530/329; 530/330; 530/350; 530/403; 530/826
[58] Field of Search ................... 435/5, 235.1; 530/324, 530/325, 326, 327, 328, 329, 330, 350, 403, 826

[56] References Cited

U.S. PATENT DOCUMENTS

| | | | |
|---|---|---|---|
| 5,218,099 | 6/1993 | Reyes et al. | 536/23.72 |
| 5,350,671 | 9/1994 | Houghton et al. | 435/5 |

FOREIGN PATENT DOCUMENTS

| | | |
|---|---|---|
| 0318216 | 5/1989 | European Pat. Off. . |
| 0363025 | 4/1990 | European Pat. Off. . |
| 0388232 | 9/1990 | European Pat. Off. . |
| 0416725 | 3/1991 | European Pat. Off. . |
| 0468527 | 1/1992 | European Pat. Off. . |
| 0468657 | 1/1992 | European Pat. Off. . |
| 0479376 | 4/1992 | European Pat. Off. . |
| 0377303 | 7/1992 | European Pat. Off. . |
| 0451891 | 10/1992 | European Pat. Off. . |
| 2239245 | 4/1991 | United Kingdom . |
| WO90/00597 | 1/1990 | WIPO . |
| WO 92/00328 | 1/1992 | WIPO . |

OTHER PUBLICATIONS

Houghton et al., *Hepatology* (1991) 14 (2):381–388.
Choo, et al., *Proc. Nat'l Acad Sci USA*, 88:2541–2455 (1991).
Kato, et al., *Proc. Nat'l Acad Sci USA*, 87: 9524–9528 (1990).
Takamizawa, et al., *J. Virol.*, 65: 1105–1113 (1991).
Okamoto, et al., *Jpn. J. Exp. Med.*, 60: 167–177 (1991).
Takeuchi, et al., *J. Gen. Virol.*, 71: 3027–3033 (1990).
Kubo, et al., *Nucleic Acids Res.*, 17: 10367–10372 (1989).
Takeuchi, et al., *Gene*, 91: 287–291 (1990).
Takeuchi, et al., *Nucleic Acids Res.*, 18: 4626 (1990).
Kato, et al., *Proc. Jpn. Acad.*, 65B: 219–223 (1989).
Maeno, et al., *Nucleic Acids Res.*, 18: 2685–2789 (1990).
Weiner, et al., *Virology*, 180: 842–848 (1991).
Putney, et al., "AIDS Vaccines Development: Current Research and Patent Considerations" *Current Antimicrobial Patents*, vol. 2, pp. 543–556 (19 ).
Tsukiyama–Kohara, et al., *Virus Genes*, 5(3): 243–253 (1991).
Enomoto, et al., *Japan Biochem Biophys Res. Commun.*, 170: 1021–1025 (1990).
Simmonds, et al., *The Lancet*, 336: 1469–1472 (1990).
Prince et al., *Ann. Rev. Micrbiol.* (1983) 37:217–232.
Feinstone et al., *New Engl. J. Med.* (1984) 311:185–189.
Overby et al., *Curr. Hepatol.* (1985) 5:49–85.
Overby et al., *Curr. Hepatol.* (1987) 7:35–67.
Iwarson, *British Med. J.* (1987) 295:946–948.
Choo et al., *Science* (1989) 244:359–262.
Overby et al., *Curr. Hepatol.* (1986) 6:65–91.
Takamizawa et al., *J. Virol.* (1991) 65:1105–1113.
Lewin *Science* (1987) 237:1570.
Reeck et al., *Cell* (1987) 50:667.
Kato et al., "Molecular cloning of the human hepatitis C virus genome from Japanese patients with non–A, non–B hepatitis", Proc. Natl. Acad. Sci. USA 87, 9524–9528 (1990).
Reanney, "The Evolution of RNA Viruses", Ann. Rev. Microbiol. 36, 47–73 (1982).

*Primary Examiner*—Michael P. Woodward
*Assistant Examiner*—Mary K. Zeman
*Attorney, Agent, or Firm*—Dale H. Hoscheit; Alisa A. Harbin; Robert P. Blackburn

[57] ABSTRACT

Two new isolates of the Hepatitis C virus (HCV), J1 and J7, are disclosed. These new isolates comprise nucleotide and amino acid sequences which are distinct from the prototype HCV isolate, HCV1. Thus, J1 and J7 provide new polynucleotides and polypeptides for use, inter alia, in diagnostics, recombinant protein production and vaccine development.

14 Claims, 23 Drawing Sheets

```
J7    1  AGCCGAGTAGTGTTGGGTCGCGAAAGGCCTTGTGGTACTGCCTGATAGGGTGCTTGCGAG   60
discrepancy
clone
altered aa MetSerThrAsnProLysProGlnArgLys
J7   61  TGCCCCGGGAGGTCTCGTAGACCGTGCATCATGAGCACAAATCCTAAACCCCAAAGAAAA  120
                                                                  TG
                                                                  b1
                                                                  ---Arg ThrLysArgAsnThrAsnArgArgProGlnAspValLysPheProGlyGlyGlyGlnIle
J7  121  ACCAAACGTAACACCAACCGTCGCCCACAGGACGTTAAGTTCCCGGGCGGTGGTCAGATC  180
                                C               T
                                b               1
                                ---            Leu ValGlyGlyValTyrLeuLeuProArgArgGlyProArgLeuGlyValArgAlaThrArg
J7  181  GTCGGTGGAGTTTACTTGTTGCCGCGCAGGGGCCCCAGGTTGGGTGTGCGTGCGACTAGG  240
          T                    A
          b                    b
         ---                  ---

LysThrSerGluArgSerGlnProArgGlyArgArgGlnProIleProLysAlaArgArg
J7  241  AAGACTTCCGAGCGGTCGCAACCTCGTGGAAGGCGACAACCTATCCCCAAGGCTCGCCGG  300
                          A
                          b
                         ---

ProGluGlyArgThrTrpAlaGlnProGlyTyrProTrpProLeuTyrGlyAsnGlyGly
J7  301  CCCGAGGGCAGGACCTGGGCTCAGCCTGGGTATCCTTGGCCCCTCTATGGCAATGAGGGC  360

LeuGlyTrpAlaGlyTrpLeuLeuSerProArgGlySerArgProSerTrpGlyProAsn
J7  361  TTGGGGTGGGCAGGATGGCTCCTGTCACCCCGCGGCTCTCGGCCTAGTTGGGGCCCCAAT  420
            A                                              T  C
            b                                              c  b
         END                                              ---Thr

AspProArgArgArgSerArgAsnLeuGlyLysValIleAspThrLeuThrCysGlyPhe
J7  421  GACCCCCGGCGTAGGTCGCGTAATTTGGGTAAGGTCATCGATACCCTTACATGCGGCTTC  480
                                                                    C
                                                                    1
                                                                   Leu

AlaAspLeuMetGlyTyrIleProLeuValGlyAlaProLeuGlyAlaAlaAlaArgAla
J7  481  GCCGACCTCATGGGGTACATTCCGCTTGTCGGCGCCCCCTTAGGGGGCGCTGCCAGGGCC  540
                                   C           C
                                   c           b
                                  ---         ---

LeuAlaHisGly
J7  541  CTGGCACATGGT  552
```

FIG. 1

```
              ProLeuValGlyAlaProLeuGlyGlyAlaAlaArgAlaLeuAlaHisGlyValArgVal
J1     1   TCCGCTCGTCGGCGCCCCCTTAGGGGGCGCTGCCAGGGCCCTGGCACATGGTGTCCGGGTT    61
discrepancy                  C
clone                                         d
altered aa                                   Ser LeuGluAspGlyValAsnTyrAlaThrGlyAsnLeuProGlyCysSerPheSerIlePhe
      62   CTGGAGGACGGCGTGAACTATGCAACAGGGAATTTGCCCGGTTGCTCTTTCTCTATCTTC    121

LeuLeuAlaLeuLeuSerCysLeuThrIleProAlaSerAlaTyrGluValArgAsnVal
     122   CTCTTGGCTCTGCTGTCCTGTTTGACCATCCCAGCTTCCGCTTATGAAGTGCGCAACGTG    181
                   A     T
                   g     d
                  ---   ---

SerGlyIleTyrHisValThrAsnAspCysSerAsnSerSerIleValTyrGluAlaAla
     182   TCCGGGATATACCATGTCACAAACGACTGCTCCAACTCAAGCATTGTGTATGAGGCGGCG    241
                     T
                     d
                    ---

AspValIleMetHisAlaProGlyCysValProCysValArgGluAsnAsnSerSerArg
     242   GACGTGATCATGCATGCCCCCGGGTGCGTGCCCTGCGTTCGGGAGAACAATTCCTCCCGT    301
                                                                  C
                                                                  d
                                                                 ---

CysTrpValAlaLeuThrProThrLeuAlaAlaArgAsnAlaSerValProThrThrThr
     302   TGCTGGGTAGCGCTCACTCCCACGCTCGCGGCCAGGAATGCCAGCGTCCCCACTACGACA    361

LeuArgArgHisValAspLeuLeuValGlyThrAlaAlaPheCysSerAlaMetTyrVal
     362   TTACGACGCCACGTCGACTTGCTCGTTGGGACGGCTGCTTTCTGCTCCGCTATGTACGTG    421
                  G
                  d
                 ---

GlyAspLeuCysGlySerValPheLeuIleSerGlnLeuPheThrPheSerProArgArg
     422   GGGGATCTCTGCGGATCTGTTTTCCTCATCTCCCAGCTGTTCACCTTCTCGCCTCGCCGG    481
                               T
                               d
                              ---

HisGluThrValGlnAspCysAsnCysSerIleTyrProGlyHisValSerGlyHisArg
     482   CATGAGACAGTACAGGACTGCAACTGCTCAATCTATCCCGGCCACGTATCAGGCCATCGC    541
                                                                     T
                                                                     c
                                                                    ---

MetAlaTrpAspMetMetMetAsnTrpSerProThrAla
     542   ATGGCTTGGGATATGATGATGAACTGGTCGCCCACGGCA    580
```

FIG.2

```
                                                     AsnTrpSerProThrAla
                                    J1         1     AACTGGTCGCCCACGGCA   18
                                    discrepancy                  !!!
                                    clone
                                    altered aa AlaLeuValValSerGlnLeuLeuArgIleProGlnAlaValMetAspMetValAlaGly
J1   19  GCCTTAGTGGTGTCGCAGTTACTCCGGATCCCACAAGCTGTCATGGACATGGTGGCGGGG    78

AlaHisTrpGlyValLeuAlaGlyLeuAlaTyrTyrSerMetValGlyAsnTrpAlaLys
J1   79  GCCCACTGGGGAGTCCTAGCGGGCCTTGCCTACTATTCCATGGTGGGGAACTGGGCTAAG   138
                      G                                A
                      i                                i
                      ---                              ---

ValLeuIleValMetLeuLeuPheAlaGlyValAspGlyHisThrArgValThrGlyGly
J1   139 GTTTTGATTGTGATGCTACTCTTTGCCGGCGTTGACGGGCATACCCGCGTGACGGGGGGG   198
                                           AG              A
                                           gg              i
                                           Ser             ---

ValGlnGlyHisValThrSerThrLeuThrSerLeuPheArgProGlyAlaSerGlnLys
J1   199 GTGCAAGGCCACGTCACCTCTACACTCACGTCCCTCTTTAGACCTGGGGCGTCCCAGAAA   258
                     T             G
                     C             i
                     ---           Ala

IleGlnLeuValAsnThrAsnGlySerTrpHisIleAsnArgThrAlaLeuAsnCysAsn
J1   259 ATTCAGCTTGTAAACACCAATGGCAGTTGGCATATCAACAGGACTGCCCTGAACTGCAAT   318
                 TC T                                          T
                 ii i                                          g
                 SerLeu                                        ---

AspSerLeuGlnThrGlyPheLeuAlaAlaLeu
J1   319 GACTCCCTCCAAACTGGGTTCCTTGCCGCGCTG   351
```

FIG.3

```
                                                       Ser
                                        J1        1    CTCA   4
                                        discrepancy
                                        clone
                                        altered aa ValIleAspCysAsnThrCysValThrGlnThrValAspPheSerLeuAspProThrPhe
J1     5    GTGATCGACTGTAACACATGTGTCACTCAGACGGTCGATTTCAGCTTGGATCCCACCTTC   64
                                                                G
                                                                C
                                                                Ala ThrIleGluThrThrThrValProGlnAspAlaValSerArgThrGlnArgArgGlyArg
J1     65   ACCATCGAGACGACGACCGTGCCCCAAGATGCGGTTTCGCGCACGCAGCGGCGAGGTAGG   124

ThrGlyArgGlyArgArgGlyIleTyrArgPheValThrProGlyGluArgProSerAla
J1     125  ACTGGCAGGGGCAGGAGAGGCATCTATAGGTTTGTGACTCCAGGAGAACGGCCCTCGGCG   184

MetPheAspSerSerValLeuCysGluCysTyrAspAlaGlyCysAlaTrpTyrGluLeu
J1     185  ATGTTCGATTCTTCGGTCCTATGTGAGTGTTATGACGCGGGCTGTGCTTGGTATGAGCTC   244
                                               A
                                               e
                                               Gly(=)

ThrProAlaGluThrSerValArgLeuArgAlaTyrLeuAsnThrProGlyLeuProVal
J1     245  ACGCCCGCTGAGACCTCGGTTAGGTTGCGGGCTTACCTAAATACACCAGGGTTGCCCGTC   304

CysGlnAspHisLeuGluPheTrpGluSerValPheThrGlyLeuThrHisIleAspAla
J1     305  TGCCAGGACCATCTGGAGTTCTGGGAGAGCGTCTTCACAGGCCTCACCCACATAGACGCC   364

HisPheLeuSerGlnThrLysGlnAlaGlyAspAsnPheProTyrLeuValAlaTyrGln
J1     365  CACTTCTTGTCCCAGACTAAGCAGGCAGGAGACAACTTCCCCTACCTGGTAGCATACCAA   424

AlaThrValCysAlaArgAlaLysAlaProProProSerTrpAspGlnMetTrpLysCys
J1     425  GCCACAGTGTGCGCCAGGGCTAAGGCTCCACCTCCATCGTGGGATCAAATGTGGAAGTGT   484
                                C
                                e
                                Ala(=)

LeuIleArgLeuLysProThrLeuHisGlyProThrProLeuLeuTyrArgLeuGlyAla
J1     485  CTCATACGGCTAAAGCCTACGCTGCACGGGCCAACGCCCCTGCTGTATAGGCTAGGAGCC   544
                                     G                        A
                                     e                        e
                                     Ala                      Arg(=)

ValGlnAsnGluValThrLeuThrHisProIleThrLys
J1     545  GTCCAGAATGAGGTCACCCTCACACACCCTATAACCAAA        583
```

FIG.4

```
                                              LeuThr
                              J1        1   CCTCACC   7
                              discrepancy
                              clone
                              altered aa ArgAspProThrValProLeuAlaArgAlaAlaTrpGluThrAlaArgHisThrProVal
J1    8    CGTGACCCCACCGTCCCCCTTGCGCGGGCTGCGTGGGAGACAGCTAGACACACTCCAGTC  67
                                                     C
                                                     g
                                                  Thr(=)

AsnSerTrpLeuGlyAsnIleIleMetTyrAlaProThrLeuTrpAlaArgMetIleLeu
J1    68   AACTCCTGGCTAGGCAACATCATCATGTATGCGCCCACTTTGTGGGCAAGGATGATTCTG    127
                            T
                            g
                          Ile(=)

MetThrHisPhePheSerIleLeuLeuAlaGlnGluGlnLeuGluLysAlaLeuAspCys
J1    128  ATGACTCACTTCTTCTCCATCCTTCTAGCCCAGGAGCAACTTGAAAAAGCCCTGGATTGT    187

GlnIleTyrGlyAlaCysTyrSerIleGluProLeuAspLeuProGlnIleIleGluArg
J1    188  CAAATCTACGGGGCCTGTTACTCCATTGAGCCACTTGACCTACCTCAGATCATTGAACGA    247

LeuHisGlyLeuSerAlaPheSerLeuHisSerTyrSerProGlyGluIleAsnArgVal
J1    248  CTCCATGGTCTTAGCGCATTTTCACTCCATAGTTACTCTCCAGGTGAGATCAATAGGGTG    307

AlaSerCysLeuArgLysLeuGlyValProProLeuArgValTrpArgHisArgAlaArg
J1    308  GCTTCATGCCTCAGGAAGCTTGGGGTACCACCCTTGCGAGTCTGGAGACATCGGGCCAGA    367

SerValArgAlaLysLeuLeuSerGlnGlyGlyArgAlaAlaThrLysGlyLysTyrLeu
J1    368  AGTGTCCGCGCTAAGCTACTGTCCCAAGGGGGGAGGGCCGCCACTTGTGGCAAGTACCTC    427
                                 G
                                 g
                              Gln(=)
```

FIG.5

```
J7    1  AGCCGAGTAGTGTTGGGTCGCGAAAGGCCTTGTGGTACTGCCTGATAGGGTGCTTGCGAG  60
HCV1

MetSerThrAsnProLysProGlnArgLys
J7   61  TGCCCCGGGAGGTCTCGTAGACCGTGCATCATGAGCACAAATCCTAAACCCCAAAGAAAA  120
HCV1                          C           G        T     A
                                                             Lys

ThrLysArgAsnThrAsnArgArgProGlnAspValLysPheProGlyGlyGlyGlnIle
J7  121  ACCAAACGTAACACCAACCGTCGCCCACAGGACGTTAAGTTCCCGGGCGGTGGTCAGATC  180
HCV1     A                                     C       T  C
         Asn
         ***

ValGlyGlyValTyrLeuLeuProArgArgGlyProArgLeuGlyValArgAlaThrArg
J7  181  GTCGGTGGAGTTTACTTGTTGCCGCGCAGGGGCCCCAGGTTGGGTGTGCGTGCGACTAGG  240
HCV1        T           T  A                        C    G  A

LysThrSerGluArgSerGlnProArgGlyArgArgGlnProIleProLysAlaArgArg
J7  241  AAGACTTCCGAGCGGTCGCAACCTCGTGGAAGGCGACAACCTATCCCCAAGGCTCGCCGG  300
HCV1                       A  T  A  T  G                          T

ProGluGlyArgThrTrpAlaGlnProGlyTyrProTrpProLeuTyrGlyAsnGluGly
J7  301  CCCGAGGGCAGGACCTGGGCTCAGCCTGGGTATCCTTGGCCCCTCTATGGCAATGAGGGC  360
HCV1                                 C     C

LeuGlyTrpAlaGlyTrpLeuLeuSerProArgGlySerArgProSerTrpGlyProAsn
J7  361  TTGGGGTGGGCAGGATGGCTCCTGTCACCCCGCGGCTCTCGGCCTAGTTGGGGCCCCAAT  420
HCV1     GC          G              T     T              C       CA
         Cys                                                      Thr
         ***                                                      ***

AspProArgArgArgSerArgAsnLeuGlyLysValIleAspThrLeuThrCysGlyPhe
J7  421  GACCCCCGGCGTAGGTCGCGTAATTTGGGTAAGGTCATCGATACCCTTACATGCGGCTTC  480
HCV1                C                                            G

AlaAspLeuMetGlyTyrIleProLeuValGlyAlaProLeuGlyGlyAlaAlaArgAla
J7  481  GCCGACCTCATGGGGTACATTCCGCTTGTCGGCGCCCCCTTAGGGGGCGCTGCCAGGGCC  540
HCV1                         A     C          TC T  A

LeuAlaHisGly
J7  541  CTGGCACATGGT  552
HCV1         G    C   781
```

```
                                           AsnTrpSerProThrAla
                         J1     1  AACTGGTCGCCCACGGCA         18
                       HCV1                C   T    A G
                                                    Thr

AlaLeuValValSerGlnLeuLeuArgIleProGlnAlaValMetAspMetValAlaGly
    J1 19 GCCTTAGTGGTGTCGCAGTTACTCCGGATCCCACAAGCTGTCATGGACATGGTGGCGGGG 78
   HCV1   G  G  AA  GT   C G                 CA  T      A C T  T
                 MetAla                              IleLeu    Ile

AlaHisTrpGlyValLeuAlaGlyLeuAlaTyrTyrSerMetValGlyAsnTrpAlaLys
    J1 79 GCCCACTGGGGAGTCCTAGCGGGCCTTGCCTACTATTCCATGGTGGGGAACTGGGCTAAG 138
   HCV1   T             G        A A  G  T TC                    T
                                    Ile    Phe

ValLeuIleValMetLeuLeuPheAlaGlyValAspGlyHisThrArgValThrGlyGly
   J1 139 GTTTTGATTGTGATGCTACTCTTTGCCGGCGTTGACGGGCATACCCGCGTGACGGGGGGG 198
   HCV1      CC   G A  C    G A       C      C  CGA A   C  C    A
             Val    Leu                         AlaGlu  His
                                                        ***

ValGlnGlyHisValThrSerThrLeuThrSerLeuPheArgProGlyAlaSerGlnLys
   J1 199 GTGCAAGGCCACGTCACCTCTACACTCACGTCCCTCTTTAGACCTGGGGCGTCCCAGAAA 258
   HCV1   AGTGCC      ACTGTG    GG T TGTTAG    C CGC   A  C  CAAG      C
         SerAla      ThrVal    GlyPheVal     LeuAla       Lys   Asn
         ******     ******    ***          ***           *** ***

IleGlnLeuValAsnThrAsnGlySerTrpHisIleAsnArgThrAlaLeuAsnCysAsn
   J1 259 ATTCAGCTTGTAAACACCAATGGCAGTTGGCATATCAACAGGACTGCCCTGAACTGCAAT 318
   HCV1   G C   GA C        C             CC    T C  G
         Val   Ile                        Leu   Ser
                                                ***

AspSerLeuGlnThrGlyPheLeuAlaAlaLeu
   J1 319 GACTCCCTCCAAACTGGGTTCCTTGCCGCGCTG 351
   HCV1   TAG    A C  C  C GGT G  A G    T
                Asn       Trp      Gly
```

FIG.8

```
          .                    .SerValIleAspCysAsnThrCysValThrGlnThrVal
   J1  1                       CTCAGTGATCGACTGTAACACATGTGTCACTCAGACGGTC
   HCV1     ggctataccggcgacttcga  G   A   C T G       C    A AspPheSerLeuAspProThrPheThrIleGluThrThrThrValProGlnAspAlaVal
   J1  41   GATTTCAgCTTGGATCCCACCTTCACCATCGAGACGACGACCGTGCCCCAAGATGCGGTT
   HCV1          C  T  C  T          T      A TC GC C       G      T  C
                                              Ile SerArgThrGlnArgArgGlyArgThrGlyArgGlyArgArgGlyIleTyrArgPheVal
   J1  101  TCGCGCACGCAGCGGCGAGGTAGGACTGGCAGGGGCAGGAGAGGCATCTATAGGTTTGTG
   HCV1       C      T A T G  C              G A CC           C  A
                                                   LysPro ThrProGlyGluArgProSerAlaMetPheAspSerSerValLeuCysGluCysTyrAsp
   J1  161  ACTCCAGGAGAACGGCCCTCGGCGATGTTCGATTCTTCGGTCCTATGTGAGTGTTATGAC
   HCV1     G A  G    G  G  C    C GC        C G  C     C         C
            Ala                 Gly AlaGlyCysAlaTrpTyrGluLeuThrProAlaGluThrSerValArgLeuArgAlaTyr
   J1  221  GCGGGCTGTGCTTGGTATGAGCTCACGCCCGCTGAGACCTCGGTTAGGTTGCGGGCTTAC
   HCV1        A                          C   TA A      C A  A   G
                                                 Thr LeuAsnThrProGlyLeuProValCysGlnAspHisLeuGluPheTrpGluSerValPhe
   J1  281  CTAAATACACCAGGGTTGCCCGTCTGCCAGGACCATCTGGAGTTCTGGGAGAGCGTCTTC
   HCV1     A G  C  C  G   CT        G         T  A T        G      T
            Met                                                  Gly ThrGlyLeuThrHisIleAspAlaHisPheLeuSerGlnThrLysGlnAlaGlyAspAsn
   J1  341  ACAGGCCTCACCCACATAGACGCCCACTTCTTGTCCCAGACTAAGCAGGCAGGAGACAAC
   HCV1            T     T     T        TC A      A    AGT G  G
                                                       Ser    Glu PheProTyrLeuValAlaTyrGlnAlaThrValCysAlaArgAlaLysAlaProProPro
   J1  401  TTCCCCTACCTGGTAGCATACCAAGCCACAGTGTGCGCCAGGGCTAAGGCTCCACCTCCA
   HCV1       C T  T        G          C        T         CA C T C
            Leu                                           Gln SerTrpAspGlnMetTrpLysCysLeuIleArgLeuLysProThrLeuHisGlyProThr
   J1  461  TCGTGGGATCAAATGTGGAAGTGTCTCATACGGCTAAAGCCTACGCTGCACGGGCCAACG
   HCV1            C  G              TG T CC     C  C  T              A ProLeuLeuTyrArgLeuGlyAlaValGlnAsnGluValThrLeuThrHisProIleThr
   J1  521  CCCCTGCTGTATAGGCTAGGAGCCGTCCAGAATGAGGTCACCCTCACACACCCTATAACC
   HCV1          A C  A G CT T       AA        G   G       AG C
                                         Ile                   Val
            Lys
   J1  581  AAA
   HCV1        tacatcatgacatgcatgtc
```

FIG.9

```
                                                              LeuThr
                                                      J1    1 CCTCACC  7
                                                      HCV1

ArgAspProThrValProLeuAlaArgAlaAlaTrpGluThrAlaArgHisThrProVal
       J1   8 CGTGACCCCACCGTCCCCCTTGCGCGGGCTGCGTGGGAGACAGCTAGACACACTCCAGTC 67
       HCV1       T   AAC      C      A A                A
                   Thr
                   ***

AsnSerTrpLeuGlyAsnIleIleMetTyrAlaProThrLeuTrpAlaArgMetIleLeu
       J1  68 AACTCCTGGCTAGGCAACATCATCATGTATGCGCCCACTTTGTGGGCAAGGATGATTCTG 127
       HCV1    T              A      T  C      AC       G         A
                                        Phe

MetThrHisPhePheSerIleLeuLeuAlaGlnGluGlnLeuGluLysAlaLeuAspCys
       J1 128 ATGACTCACTTCTTCTCCATCCTTCTAGCCCAGGAGCAACTTGAAAAAGCCCTGGATTGT 187
       HCV1      C  T       TAG G   A      AG  C   G          CG    C  C
                            Val    Ile     ArgAsp              Gln
                                           ***                 ***

GlnIleTyrGlyAlaCysTyrSerIleGluProLeuAspLeuProGlnIleIleGluArg
       J1 188 CAAATCTACGGGGCCTGTTACTCCATTGAGCCACTTGACCTACCTCAGATCATTGAACGA 247
       HCV1   G G           C         A  A      T        CA       C  A
              Glu                                        Pro      Gln
              ***                                        ***      ***

LeuHisGlyLeuSerAlaPheSerLeuHisSerTyrSerProGlyGluIleAsnArgVal
       J1 248 CTCCATGGTCTTAGCGCATTTTCACTCCATAGTTACTCTCCAGGTGAGATCAATAGGGTG 307
       HCV1           C  C                C                    A T

AlaSerCysLeuArgLysLeuGlyValProProLeuArgValTrpArgHisArgAlaArg
       J1 308 GCTTCATGCCTCAGGAAGCTTGGGGTACCACCCTTGCGAGTCTGGAGACATCGGGCCAGA 367
       HCV1      CG       A  A         G          CT       C      C G
                Ala                                Ala
                ***                                ***

SerValArgAlaLysLeuLeuSerGlnGlyGlyArgAlaAlaThrLysGlyLysTyrLeu
       J1 368 AGTGTCCGCGCTAAGCTACTGTCCCAAGGGGGGAGGCCGCCACTTGTGGCAAGTACCTC 427
       HCV1      C        G     T     G  AG   A   C        TA      Ile
                          Arg         AlaArg                ***
                                      ***
```

FIG. 10

```
                                                    --------
CACTCCACCATGAATCACTCCCCTGTGAGGAACTACTGTCTTCACGCAGAAAGCGTCTAG
CCATGGCGTTAGTATGAGTGTCGTGCAGCCTCCAGGACCCCCCCTCCCGGGAGAGCCATA
GTGGTCTGCGGAACCGGTGAGTACACCGGAATTGCCAGGACGACCGGGTCCTTTCTTGGA
TCAACCCGCTCAATGCCTGGAGATTTGGGCGTGCCCCCGCAAGACTGCTAGCCGAGTAGT
GTTGGGTCGCGAAAGGCCTTGTGGTACTGCCTGATACGGTGCTTGCGAGTGCCCCGGGAG-300
                        ---(Putative initiator methionine codon)
GTCTCGTAGACCGTGCACCATGAGCACGAATCCTAAACCTCAAAAAAAAAACAAACGTAA
CACCAACCGTCGCCCACAGGACGTCAAGTTCCCGGGTGGCGGTCAGATCGTTGGTGGAGT
TTACTTGTTGCCGCGCAGGGGCCCTAGATTGGGTGTGCGCGCGACGAGAAAGACTTCCGA
GCGGTCGCAACCTCGAGGTAGACGTCAGCCTATCCCCAAGGCTCGTCGGCCCGAGGGCAG
GACCTGGGCTCAGCCCGGGTACCCTTGGCCCCTCTATGGCAATGAGGGCTGCGGGTGGGC-600
GGGATGGCTCCTGTCTCCCCGTGGCTCTCGGCCTAGCTGGGGCCCCACAGACCCCCGGCG
TAGGTCGCGCAATTTGGGTAAGGTCATCGATACCCTTACGTGCGGCTTCGCCGACCTCAT
GGGGTACATACCGCTCGTCGGCGCCCCTCTTGGAGGCGCTGCCAGGGCCCTGGCGCATGG
CGTCCGGGTTCTGGAAGACGGCGTGAACTATGCAACAGGGAACCTTCCTGGTTGCTCTTT
CTCTATCTTCCTTCTGGCCCTGCTCTCTTGCTTGACTGTGCCCGCTTCGGCCTACCAAGT-900
GCGCAACTCCACGGGGCTTTACCACGTCACCAATGATTGCCCTAACTCGAGTATTGTGTA
CGAGGCGGCCGATGCCATCCTGCACACTCCGGGGTGCGTCCCTTGCGTTCGTGAGGGCAA
CGCCTCGAGGTGTTGGGTGGCGATGACCCCTACGGTGGCCACCAGGGATGGCAAACTCCC
CGCGACGCAGCTTCGACGTCACATCGATCTGCTTGTCGGGAGCGCCACCCTCTGTTCGGC
CCTCTACGTGGGGGACCTATGCGGGTCTGTCTTTCTTGTCGGCCAACTGTTCACCTTCTC-1200
TCCCAGGCGCCACTGGACGACGCAAGGTTGCAATTGCTCTATCTATCCCGGCCATATAAC
GGGTCACCGCATGGCATGGGATATGATGATGAACTGGTCCCCTACGACGGCGTTGGTAAT
GGCTCAGCTGCTCCGGATCCCACAAGCCATCTTGGACATGATCGCTGGTGCTCACTGGGG
AGTCCTGGCGGGCATAGCGTATTTCTCCATGGTGGGGAACTGGGCGAAGGTCCTGGTAGT
GCTGCTGCTATTTGCCGGCGTCGACGCGGAAACCCACGTCACCGGGGGAAGTGCCGGCCA-1500
CACTGTGTCTGGATTTGTTAGCCTCCTCGCACCAGGCGCCAAGCAGAACGTCCAGCTGAT
CAACACCAACGGCAGTTGGCACCTCAATAGCACGGCCCTGAACTGCAATGATAGCCTCAA
CACCGGCTGGTTGGCAGGGCTTTTCTATCACCACAAGTTCAACTCTTCAGGCTGTCCTGA
GAGGCTAGCCAGCTGCCGACCCCTTACCGATTTTGACCAGGGCTGGGGCCCTATCAGTTA
TGCCAACGGAAGCGGCCCCGACCAGCGCCCTACTGCTGGCACTACCCCCAAAACCTTG-1800
CGGTATTGTGCCCGCGAAGAGTGTGTGTGGTCCGGTATATTGCTTCACTCCCAGCCCCGT
GGTGGTGGGAACGACCGACAGGTCGGGCGCGCCCACCTACAGCTGGGGTGAAAATGATAC
GGACGTCTTCGTCCTTAACAATACCAGGCCACCGCTGGGCAATTGGTTCGGTTGTACCTG
GATGAACTCAACTGGATTCACCAAAGTGTGCGGAGCGCCTCCTTGTGTCATCGGAGGGGC
GGGCAACAACACCCTGCACTGCCCCACTGATTGCTTCCGCAAGCATCCGGACGCCACATA-2100
CTCTCGGTGCGGCTCCGGTCCCTGGATCACACCCAGGTGCCTGGTCGACTACCCGTATAG
GCTTTGGCATTATCCTTGTACCATCAACTACACCATATTTAAAATCAGGATGTACGTGGG
AGGGGTCGAACACAGGCTGGAAGCTGCCTGCAACTGGACGCGGGGCGAACGTTGCGATCT
GGAAGACAGGGACAGGTCCGAGCTCAGCCCGTTACTGCTGACCACTACACAGTGGCAGGT
CCTCCCGTGTTCCTTCACAACCCTACCAGCCTTGTCCACCGGCCTCATCCACCTCCACCA-2400
GAACATTGTGGACGTGCAGTACTTGTACGGGGTGGGGTCAAGCATCGCGTCCTGGGCCAT
TAAGTGGGAGTACGTCGTTCTCCTGTTCCTTCTGCTTGCAGACGCGCGCGTCTGCTCCTG
CTTGTGGATGATGCTACTCATATCCCAAGCGGAGGCGGCTTTGGAGAACCTCGTAATACT
TAATGCAGCATCCCTGGCCGGGACGCACGGTCTTGTATCCTTCCTCGTGTTCTTTCTGCTT
TGCATGGTATTTGAAGGGTAAGTGGGTGCCCGGACGGGTCTACACCTTCTACGGGATGTG-2700
GCCTCTCCTCCTGCTCCTGTTGGCGTTGCCCCAGCGGGCGTACGCGCTGGACACGGAGGT
GGCCGCGTCGTGTGGCGGTGTTGTTCTCGTCGGGTTGATGGCGCTGACTCTGTCACCATA
TTACAAGCGCTATATCAGCTGGTGCTTGTGGTGGCTTCAGTATTTTCTGACCAGAGTGGA
AGCGCAACTGCACGTGTGGATTCCCCCCTCAACGTCCGAGGGGGCGCGACGCCGTCAT
CTTACTCATGTGTGCTGTACACCCGACTCTGGTATTTGACATCACCAAATTGCTGCTGGC-3000
```

FIG. 12A

```
CGTCTTCGGACCCCTTTGGATTCTTCAAGCCAGTTTGCTTAAAGTACCCTACTTTGTGCG
CGTCCAAGGCCTTCTCCGGTTCTGCGCGTTAGCGCGGAAGATGATCGGAGGCCATTACGT
GCAAATGGTCATCATTAAGTTAGGGGCGCTTACTGGCACCTATGTTTATAACCATCTCAC
TCCTCTTCGGGACTGGGCGCACAACGGCTTGCGAGATCTGGCCGTGGCTGTAGAGCCAGT
CGTCTTCTCCCAAATGGAGACCAAGCTCATCACGTGGGGGGCAGATACCGCCGCGTGCGG-3300
TGACATCATCAACGGCTTGCCTGTTTCCGCCCGCAGGGGCCGGGAGATACTGCTCGGGCC
AGCCGATGGAATGGTCTCCAAGGGGTGGAGGTTGCTGGCGCCCATCACGGCGTACGCCCA
GCAGACAAGGGGCCTCCTAGGGTGCATAATCACCAGCCTAACTGGCCGGGACAAAAACCA
AGTGGAGGGTGACGTCCAGATTGTGTCAACTGCTGCCCAAACCTTCCTGGCAACGTGCAT
CAATGGGGTGTGCTGGACTGTCTACCACGGGGCCGGAACGAGGACCATCGCGTCACCCAA-3600
GGGTCCTGTCATCCAGATGTATACCAATGTAGACCAAGACCTTGTGGGCTGGCCCGCTCC
GCAAGGTAGCCGCTCATTGACACCCTGCACTTGCGGCTCCTCGGACCTTTACCTGGTCAC
GAGGCACGCCGATGTCATTCCCGTGCGCCGGCGGGGTGATAGCAGGGGCAGCCTGCTGTC
GCCCCGGCCCATTTCCTACTTGAAAGGCTCCTCGGGGGGTCCGCTGTTGTGCCCCGCGGG
GCACGCCGTGGGCATATTTAGGGCCGCGGTGTGCACCCGTGGAGTGGCTAAGGCGGTGGA-3900
CTTTATCCCTGTGGAGAACCTAGAGACAACCATGAGGTCCCCGGTGTTCACGGATAACTC
CTCTCCACCAGTAGTGCCCCAGAGCTTCCAGGTGGCTCACCTCCATGCTCCCACAGGCAG
CGGCAAAAGCACCAAGGTCCCGGCTGCATATGCAGCTCAGGGCTATAAGGTGCTAGTACT
CAACCCTCTGTTGCTGCAACACTGGGCTTTGGTGCTTACATGTCCAAGGCTCATGGGAT
CGATCCTAACATCAGGACCGGGGTGAGAACAATTACCACTGGCAGCCCCATCACGTACTC-4200
CACCTACGGCAAGTTCCTTGCCGACGGCGGGTGCTCGGGGGGCGCTTATGACATAATAAT
TTGTGACGAGTGCCACTCCACGGATGCCACATCCATCTTGGGCATCGGCACTGTCCTTGA
CCAAGCAGAGACTGCGGGGGCGAGACTGGTTGTGCTCGCCACCGCCACCCCTCCGGGCTC
CGTCACTGTGCCCCATCCCAACATCGAGGAGGTTGCTCTGTCCACCACCGGAGAGATCCC
TTTTTACGGCAAGGCTATCCCCCTCGAAGTAATCAAGGGGGGGAGACATCTCATCTTCTG-4500
TCATTCAAAGAAGAAGTGCGACGAACTCGCCGCAAAGCTGGTCGCATTGGGCATCAATGC
CGTGGCCTACTACCGCGGTCTTGACGTGTCCGTCATCCCGACCAGCGGCGATGTTGTCGT
CGTGGCAACCGATGCCCTCATGACCGGCTATACCGGCGACTTCGACTCGGTGATAGACTG
CAATACGTGTGTCACCCAGACAGTCGATTTCAGCCTTGACCCTACCTTCACCATTGAGAC
AATCACGCTCCCCCAGGATGCTGTCTCCCGCACTCAACGTCGGGGCAGGACTGGCAGGGG-4800
GAAGCCAGGCATCTACAGATTTGTGGCACCGGGGGAGCGCCCCTCCGGCATGTTCGACTC
GTCCGTCCTCTGTGAGTGCTATGACGCAGGCTGTGCTTGGTATGAGCTCACGCCCGCCGA
GACTACAGTTAGGCTACGAGCGTACATGAACACCCCGGGGCTTCCCGTGTGCCAGGACCA
TCTTGAATTTTGGGAGGGCGTCTTTACAGGCCTCACTCATATAGATGCCCACTTTCTATC
CCAGACAAAGCAGAGTGGGGAGAACCTTCCTTACCTGGTAGCGTACCAAGCCACCGTGTG-5100
CGCTAGGGCTCAAGCCCCTCCCCCATCGTGGGACCAGATGTGGAAGTGTTTGATTCGCCT
CAAGCCCACCCTCCATGGGCCAACACCCCTGCTATACAGACTGGGCGCTGTTCAGAATGA
AATCACCCTGACGCACCCAGTCACCAAATACATCATGACATGCATGTCGGCCGACCTGGA
GGTCGTCACGAGCACCTGGGTGCTCGTTGGCGGCGTCCTGGCTGCTTTGGCCGCGTATTG
CCTGTCAACAGGCTGCGTGGTCATAGTGGGCAGGGTCGTCTTGTCCGGGAAGCCGGCAAT-5400
CATACCTGACAGGGAAGTCCTCTACCGAGAGTTCGATGAGATGGAAGAGTGCTCTCAGCA
CTTACCGTACATCGAGCAAGGGATGATGCTCGCCGAGCAGTTCAAGCAGAAGGCCCTCGG
CCTCCTGCAGACCGCGTCCCGTCAGGCAGAGGTTATCGCCCCTGCTGTCCAGACCAACTG
GCAAAAACTCGAGACCTTCTGGGCGAAGCATATGTGGAACTTCATCAGTGGGATACAATA
CTTGGCGGGCTTGTCAACGCTGCCTGGTAACCCCGCCATTGCTTCATTGATGGCTTTTAC-5700
AGCTGCTGTCACCAGCCCACTAACCACTAGCCAAACCCTCCTCTTCAACATATTGGGGGG
GTGGGTGGCTGCCCAGCTCGCCGCCCCGGTGCCGCTACTGCCTTTGTGGGCGCTGGCTT
AGCTGGCGCCGCCATCGGCAGTGTTGGACTGGGGAAGGTCCTCATAGACATCCTTGCAGG
GTATGGCGCGGGCGTGGCGGGAGCTCTTGTGGCATTCAAGATCATGAGCGGTGAGGTCCC
CTCCACGGAGGACCTGGTCAATCTACTGCCCGCCATCCTCTCGCCCGGAGCCCTCGTAGT-6000
```

FIG. 12B

```
CGGCGTGGTCTGTGCAGCAATACTGCGCCGGCACGTTGGCCCGGGCGAGGGGGCAGTGCA
GTGGATGAACCGGCTGATAGCCTTCGCCTCCCGGGGGAACCATGTTTCCCCCACGCACTA
CGTGCCGGAGAGCGATGCAGCTGCCCGCGTCACTGCCATACTCAGCAGCCTCACTGTAAC
CCAGCTCCTGAGGCGACTGCACCAGTGGATAAGCTCGGAGTGTACCACTCCATGCTCCGG
TTCCTGGCTAAGGGACATCTGGGACTGGATATGCGAGGTGTTGAGCGACTTTAAGACCTG-6300
GCTAAAAGCTAAGCTCATGCCACAGCTGCCTGGGATCCCCTTTGTGTCCTGCCAGCGCGG
GTATAAGGGGGTCTGGCGAGTGGACGGCATCATGCACACTCGCTGCCACTGTGGAGCTGA
GATCACTGGACATGTCAAAAACGGGACGATGAGGATCGTCGGTCCTAGGACCTGCAGGAA
CATGTGGAGTGGGACCTTCCCCATTAATGCCTACACCACGGGCCCCTGTACCCCCCTTCC
TGCGCCGAACTACACGTTCGCGCTATGGAGGGTGTCTGCAGAGGAATATGTGGAGATAAG-6600
GCAGGTGGGGACTTCCACTACGTGACGGGTATGACTACTGACAATCTCAAATGCCCGTG
CCAGGTCCCATCGCCCGAATTTTTCACAGAATTGGACGGGGTGCGCCTACATAGGTTTGC
GCCCCCTGCAAGCCCTTGCTGCGGGAGGAGGTATCATTCAGAGTAGGACTCCACGAATA
CCCGGTAGGGTCGCAATTACCTTGCGAGCCCGAACCGGACGTGGCCGTGTTGACGTCCAT
GCTCACTGATCCCTCCCATATAACAGCAGAGGCGGCCGGGCGAAGGTTGGCGAGGGGATC-6900
ACCCCCCTCTGTGGCCAGCTCCTCGGCTAGCCAGCTATCCGCTCCATCTCTCAAGGCAAC
TTGCACCGCTAACCATGACTCCCCTGATGCTGAGCTCATAGAGGCCAACCTCCTATGGAG
GCAGGAGATGGGCGGCAACATCACCAGGGTTGAGTCAGAAAACAAAGTGGTGATTCTGGA
CTCCTTCGATCCGCTTGTGGCGGAGGAGGACGAGCGGGAGATCTCCGTACCCGCAGAAAT
CCTGCGGAAGTCTCGGAGATTCGCCCAGGCCCTGCCCGTTTGGGCGCGGCCGGACTATAA-7200
CCCCCCGCTAGTGGAGACGTGGAAAAAGCCCGACTACGAACCACCTGTGGTCCATGGCTG
TCCGCTTCCACCTCCAAAGTCCCCTCCTGTGCCTCCGCCTCGGAAGAAGCGGACGGTGGT
CCTCACTGAATCAACCCTATCTACTGCCTTGGCCGAGCTCGCCACCAGAAGCTTTGGCAG
CTCCTCAACTTCCGGCATTACGGGCGACAATACGACAACATCCTCTGAGCCCGCCCCTTC
TGGCTGCCCCCCCGACTCCGACGCTGAGTCCTATTCCTCCATGCCCCCCCTGGAGGGGGA-7500
GCCTGGGGATCCGGATCTTAGCGACGGGTCATGGTCAACGGTCAGTAGTGAGGCCAACGC
GGAGGATGTCGTGTGCTGCTCAATGTCTTACTCTTGGACAGGCGCACTCGTCACCCCGTG
CGCCGCGGAAGAACAGAAACTGCCCATCAATGCACTAAGCAACTCGTTGCTACGTCACCA
CAATTTGGTGTATTCCACCACCTCACGCAGTGCTTGCCAAAGGCAGAAGAAAGTCACATT
TGACAGACTGCAAGTTCTGGACAGCCATTACCAGGACGTACTCAAGGAGGTTAAAGCAGC-7800
GGCGTCAAAAGTGAAGGCTAACTTGCTATCCGTAGAGGAAGCTTGCAGCCTGACGCCCCC
ACACTCAGCCAAATCCAAGTTTGGTTATGGGGCAAAAGACGTCCGTTGCCATGCCAGAAA
GGCCGTAACCCACATCAACTCCGTGTGGAAAGACCTTCTGGAAGACAATGTAACACCAAT
AGACACTACCATCATGGCTAAGAACGAGGTTTTCTGCGTTCAGCCTGAGAAGGGGGGTCG
TAAGCCAGCTCGTCTCATCGTGTTCCCCGATCTGGGCGTGCGCGTGTGCGAAAAGATGGC-8100
TTTGTACGACGTGGTTACAAAGCTCCCCTTGGCCGTGATGGGAAGCTCCTACGGATTCCA
ATACTCACCAGGACAGCGGGTTGAATTCCTCGTGCAAGCGTGGAAGTCCAAGAAAACCCC
AATGGGGTTCTCGTATGATACCCGCTGCTTTGACTCCACAGTCACTGAGAGCGACATCCG
TACGGAGGAGGCAATCTACCAATGTTGTGACCTCGACCCCCAAGCCCGCGTGGCCATCAA
GTCCCTCACCGAGAGGCTTTATGTTGGGGCCCTCTTACCAATTCAAGGGGGAGAACTG-8400
CGGCTATCGCAGGTGCCGCGCGAGCGGCGTACTGACAACTAGCTGTGGTAACACCCTCAC
TTGCTACATCAAGGCCCGGGCAGCCTGTCGAGCCGCAGGGCTCCAGGACTGCACCATGCT
CGTGTGTGGCGACGACTTAGTCGTTATCTGTGAAAGCGCGGGGGTCCAGGAGGACGCGGC
GAGCCTGAGAGCCTTCACGGAGGCTATGACCAGGTACTCCGCCCCCCCTGGGGACCCCCC
ACAACCAGAATACGACTTGGAGCTCATAACATCATGCTCCTCCAACGTGTCAGTCGCCCA-8700
CGACGGCGCTGGAAAGAGGGTCTACTACCTCACCCGTGACCCTACAACCCCCCTCGCGAG
AGCTGCGTGGGAGACAGCAAGACACACTCCAGTCAATTCCTGGCTAGGCAACATAATCAT
GTTTGCCCCCACACTGTGGGCGAGGATGATACTGATGACCCATTTCTTTAGCGTCCTTAT
AGCCAGGGACCAGCTTGAACAGGCCCTCGATTGCGAGATCTACGGGGCCTGCTACTCCAT
AGAACCACTTGATCTACCTCCAATCATTCAAAGACTCCATGGCCTCAGCGCATTTTCACT-9000
CCACAGTTACTCTCCAGGTGAAATTAATAGGGTGGCCGCATGCCTCAGAAAACTTGGGGT
ACCGCCCTTGCGAGCTTGGAGACACCGGGCCCGGAGCGTCCGCGCTAGGCTTCTGGCCAG
AGGAGGCAGGGCTGCCATATGTGGCAAGTACCTCTTCAACTGGGCAGTAAGAACAAAGCT
CAAAC
```

FIG.12C

```
                                                              primer J159S
                                                 J1   ACTGCCCTGAACTGCAATGA
                                                 PT        G SerLeuLysThrGlyPheLeuAlaAlaLeuPheTyrThrHisLysPheAsnAlaSerGl
J1    1   CTCCCTCAAAAACTGGGTTTCTTGCCGCGCTGTTCTACACACACAAGTTCAACGCGTCCGG   60
PT        TAG      C  C   C_GCT G  A G    T    TCAC             T T   A
               Asn      Trp      Gly           His              Ser
                                          primer 166A for J1-1216 yCysProGluArgMetAlaSerCysArgSerIleAspLysPheAspGlnGlyTrpGlyPr
J1   61   ATGCCCGGAGCGCATGGCCAGCTGTCGCTCCATTGACAAGTTCGACCAGGGATGGGGTCC   120
PT        C  T  T    A GC A         C  AC  C  AC GT  T         C    C
                      Leu               ProLeuThrAsp oIleThrTyrAlaGlnProAspAsnSerAspGlnArgProTyrCysTrpHisTyrAlaPr
J1   121  CATCACCTATGCTCAACCTGACAACTCCCACCACAGGCCCTATTGCTGGCACTACGCACC   180
PT        T    GT     CA  CGGAAG GG C C    C   C   C              C C
               Ser       AsnGlySerGlyPro                            Pro oArgGlnCysGlyIleValProAlaSerGlnValCysGlyProValTyrCysPheThrPr
J1   181  TCGACAGTGTGGTATCGTACCCGCGTCGCAGGTGTGCGGTCCAGTGTATTGCTTCACCCC   240
PT        AAA  CT  C      T  G       AA AGT   T     G  A            T
          LysPro              LysSer oSerProValValValGlyThrThrAspArgPheGlyAlaProThrTyrAsnTrpGlyAs
J1   241  AAGCCCTGTTGTAGTGGGGACGACCGATCGTTTCGGCGCCCCTACGTATAACTGGGGGGA   300
PT        C    C  G G    A          CA G CG     G    C    CG        T
                                       Ser              Ser        Gl pAsnGluThrAspValLeuLeuLeuAsnAsnThrArgProProHisGlyAsnTrpPheGl
J1   301  CAATGAGACGGACGTGCTGCTCCTAAACAACACGCGGCCCCCGCACGGCAACTGGTTCGG   360
PT        A   T       CT CG   T     T  CA    A      TG       T
          u   Asp        PheVal                                 Leu yCysThr
J1   361  CTGTACA  367
PT        T        CTGGATGAACTCAACTGGATT
                      primer 199A Nucleotide Match:             259/367  (70.6%)
              Amino Acid Match (stringent):  93/122  (76.2%)
                               (relaxed):   111/122  (91.0%)
```

FIG.13

```
                                                          ProLeuVal
J1                                                        TCCGCTCGTC
HCV-1                                                     A---------

GlyAlaProLeuGlyGlyAlaAlaArgAlaLeuAlaHisGlyValArgValLeuGluAsp
J1   11 GGCGCCCCCTTAGGGGGCGCTGCCAGGGCCCTGGCACATGGTGTCCGGGTTCTGGAGGAC
        ---------TC-T---A--------------------G-----C--------------A---

GlyValAsnTyrAlaThrGlyAsnLeuProGlyCysSerPheSerIlePheLeuLeuAla
J1   71 GGCGTGAACTATGCAACAGGGAATTTGCCCGGTTGCTCTTTCTCTATCTTCCTCTTGGCT
        ------------------CC-T---T---------------------------TC-----

LeuLeuSerCysLeuThrIleProAlaSerAlaTyrGluValArgAsnValSerGlyIle
J1  131 CTGCTGTCCTGTTTGACCATCCCAGCTTCCGCTTATGAAGTGCGCAACGTGTCCGGGATA
        -----C--T--C------TG-G--C------G--C--CC-----------TCCA-G---C-T
                Val                 Gln           SerThr      Leu

TyrHisValThrAsnAspCysSerAsnSerSerIleValTyrGluAlaAlaAspValIle
J1  191 TACCATGTCACAAACGACTGCTCCAACTCAAGCATTGTGTATGAGGCGGCGGACGTGATC
        -----C-----C--T---C-T------G--T---------C---------C--T-CC---
                              Pro                                 Ala

MetHisAlaProGlyCysValProCysValArgGluAsnAsnSerSerArgCysTrpVal
J1  251 ATGCATGCCCCCGGGTGCGTGCCCTGCGTTCGGGAGAACAATTCCTCCCGTTGCTGGGTA
        C----CA-T--G---------C--T---------T---GG---CG----GA-G--T-----A
        Leu  Thr                                  Gly     Ala

AlaLeuThrProThrLeuAlaAlaArgAsnAlaSerValProThrThrThrLeuArgArg
J1  311 GCGCTCACTCCCACGCTCGCGGCCAGGAATGCCAGCGTCCCCACTACGACATTACGACGC
        ---A-G---C--T---G-G--CA------G-----G---AAC-----G-G----CAGC-T-----T
        Met     Val   Thr   AspGlyLysLeu     Ala    Gln

HisValAspLeuLeuValGlyThrAlaAlaPheCysSerAlaMetTyrValGlyAspLeu
J1  371 CACGTCGACTTGCTCGTTGGGACGGCTGCTTTCTGCTCCGCTATGTACGTGGGGGATCTC
        ---A-----TC-----T--C-----GC--CA-CC----T--G--CC-C-----------C--A
        Ile         Ser        ThrLeu        Leu

CysGlySerValPheLeuIleSerGlnLeuPheThrPheSerProArgArgHisGluThr
J1  431 TGCGGATCTGTTTTCCTCATCTCCCAGCTGTTCACCTTCTCGCCTCGCCGGCATGAGACA
        -----G------C--T--TG--GG---A-----------T---CA-G--C--CTG---G
                       ValGly                                  Trp

ValGlnAspCysAsnCysSerIleTyrProGlyHisValSerGlyHisArgMetAlaTrp
J1  491 GTACAGGACTGCAACTGCTCAATCTATCCCGGCCACGTATCAGGCCATCGCATGGCTTGG
        ACG--A-GT-----T-----T---------TA--A-G--T--C--------A---
        Thr  Gly.                            IleThr

AspMetMetMetAsnTrpSerProThrAlaAlaLeuValValSerGlnLeuLeuArgIle
J1  551 GATATGATGATGAACTGGTCGCCCACGGCAGCCTTAGTGGTGTCGCAGTTACTCCGGATC
        ------------------C--T---A-G--G--AA--G-T---C-G--------
                          Thr       MetAla
```

FIG. 14A

```
                ProGlnAlaValMetAspMetValAlaGlyAlaHisTrpGlyValLeuAlaGlyLeuAla
J1    611       CCACAAGCTGTCATGGACATGGTGGCGGGGGCCCACTGGGGAGTCCTAGCGGGCCTTGCC
                --------CA--T--------A-C--T--T--T--------------G-------A-A--G
                        IleLeu      Ile                                  Ile

TyrTyrSerMetValGlyAsnTrpAlaLysValLeuIleValMetLeuLeuPheAlaGly
J1    671       TACTATTCCATGGTGGGGAACTGGGCTAAGGTTTTGATTGTGATGCTACTCTTTGCCGGC
                --T-TC--------------------G-----CC--G-A---C----G--A---------
                    Phe                              Val   Leu

ValAspGlyHisThrArgValThrGlyGlyValGlnGlyHisValThrSerThrLeuThr
J1    731       GTTGACGGGCATACCCGCGTGACGGGGGGGGTGCAAGGCCACGTCACCTCTACACTCACG
                --C-----C-G-A----A---C--C-----AAGTGCC------ACTGTG---GGAT-TGTT
                     AlaGlu     His            SerAla        ThrVal    GlyPheVal

SerLeuPheArgProGlyAlaSerGlnLysIleGlnLeuValAsnThrAsnGlySerTrp
J1    791       TCCCTCTTTAGACCTGGGGCGTCCCAGAAAATTCAGCTTGTAAACACCAATGGCAGTTGG
                AG----C-CGC---A--C--CAAGC----CG-C-----GA-C---------C--------
                      LeuAla        Lys         AsnVal       Ile

HisIleAsnArgThrAlaLeuAsnCysAsnAspSerLeuGlnThrGlyPheLeuAlaAla
J1    851       CATATCAACAGGACTGCCCTGAACTGCAATGACTCCCTCCAAACTGGGTTCCTTGCCGCG
                --CC----T--C--G----------------TAG----A-C--C--C-GGT-G--A-G-
                    Ser                        Asn             Trp      Gly

J1    911       CTGTTCTACACACACAAGTTCAACGCGTCCGGATGCCCGGAGCGCATGGCCAGCTGTCGC
                --T------TCACC-----------T-T--A--C--T--T----A-GC-A--------G--A
                        His             Ser                       Leu

SerIleAspLysPheAspGlnGlyTrpGlyProIleThrTyrAlaGlnProAspAsnSer
J1    971       TCCATTGACAAGTTCGACCAGGGATGGGGTCCCATCACCTATGCTCAACCTGACAACTCG
                C--C--AC-G-T--T---------C-----C--T----GT-----CAACGGAAGCGG-C-C
                ProLeuThrAsp                         Ser     AsnGlySerGlyPro

AspGlnArgProTyrCysTrpHisTyrAlaProArgGlnCysGlyIleValProAlaSer
J1    1031      GACCAGAGGCCGTATTGCTGGCACTACGCACCTCGACAGTGTGGTATCGTACCCGCGTCG
                ------C-C--C--C-------------C-C--AAA--CT--C-----T--G------AA-
                                             Pro   LysPro                 Lys

GlnValCysGlyProValTyrCysPheThrProSerProValValValGlyThrThrAsp
J1    1091      CAGGTGTGCGGTCCAGTGTATTGCTTCACCCCAAGCCCTGTTGTAGTGGGGACGACCGAT
                AGT-----T-----G--A------------T--C-----C--G--G-----A--------
                Ser

ArgPheGlyAlaProThrTyrAsnTrpGlyAspAsnGluThrAspValLeuLeuLeuAsn
J1    1151      CGTTTCGGCGCCCCTACGTATAACTGGGGGGACAATGAGACGGACGTGCTGCTCCTAAAC
                A-G-CG-----G--C--C--C-G------T--A-----T--------CT-CG----T---
                    Ser            Ser        Glu  Asp          PheVal

AsnThrArgProProHisGlyAsnTrpPheGlyCysThr
J1    1211      AACACGCGGCCCCCGCACGGCAACTGGTTCGGCTGTACA
                --T--CA----A----TG-----T---------T-----
                         Leu
```

FIG. 14B

```
ThrTrpMetAsnSerThrGlyPheThrLysThrCysGlyGlyProProCysAsnIleGly
ACATGGATGAATAGCACTGGGTTCACCAAGACATGCGGAGGCCCCCCGTGTAACATCGGG

GlyValGlyAsnAsnThrLeuThrCysProThrAspCysPheArgLysHisProGluAla
GGGGTCGGCAACAACACCTTGACCTGCCCCACGGACTGTTTCCGGAAGCACCCCGAGGCC

ThrTyrThrArgCysGlySerGlyProTrpLeuThrProArgCysLeuValAspTyrPro
ACTTACACAAGATGTGGTTCGGGCCCTTGGTTGACACCTAGGTGCTTGGTTGACTACCCA

TyrArgLeuTrpHisTyrProCysThrValAsnPheThrIlePheLysValArgMetTyr
TACAGGCTCTGGCACTACCCCTGCACTGTCAACTTTACCATCTTCAAGGTTAGGATGTAT

ValGlyGlyValGluHisArgLeu
GTGGGGGGCGTGGAGCACAGGCTC
```

FIG.15

```
              LeuGlyAsnTrpPheGlyCysThrTrpMetAsnSerSerGlyPheThrLysValCysGly
J1     1   GTTGGGCAATTGGTTCGGTTGCACCTGGATGAACTCATCTGGATTTACCAAAGTGTGCGG
HCV-1      -C-------------------T----------------A-------C-------------
                                                        Thr

AlaProProCysValIleGlyGlyValGlyAsnAsnThrLeuGlnCysProThrAspCys
J1    61   AGCGCCTCCTTGTGTCATCGGAGGGGTGGGCAACAACACCTTGCAATGCCCCACTGACTG
HCV-1      ------------------------C--------------C----C-----------T--
                                    Ala                 His

PheArgLysHisProAspAlaThrTyrSerArgCysGlySerGlyProTrpIleThrPro
J1   121   TTTCCGCAAGCATCCGGACGCCACATACTCTCGGTGCGGTTCCGGTCCCTGGATTACGCC
HCV-1      -------------------------------------C---------------C--A--

ArgCysLeuValHisTyrProTyrArgLeuTrpHisTyrProCysThrValAsnTyrThr
J1   181   CAGGTGCCTGGTCCACTACCCTTATAGGCTTTGGCATTATCCCTGTACTGTCAACTACAC
HCV-1      -------------G-------G--------------------T-----CA---------
                         Asp                              Ile

LeuPheLysValArgMetTyrValGlyGlyValGluHisArgLeuGluValAlaCysAsn
J1   241   CTTGTTCAAAGTCAGGATGTACGTGGGAGGGGTCGAGCACAGGCTGGAAGTTGCTTGCAA
HCV-1      -A-A--T---A-----------------------A---------------C---C-----
            Ile     Ile                                          Ala

TrpThrArgGlyGluArgCysAspLeuAspAspArgAsp
J1   301   CTGGACGCGGGGCGAGCGTTGTGATCTGGACGACAGGGACA
HCV-1      ----------------A-----C--------A---------
                            Glu
```

FIG.17

```
                              AsnMetSerLysAlaHisGlyThrAspProAsnIleArgThr
C200              3799        AATATGTCCAAGGCACATGGCACCGACCCCAACATCAGAACT
HCV-1    3781    ACACTGGGCTTTGGTGCTT-C-----------T-----G-T---T--------G--C
                 ThrLeuGlyPheGlyAlaTyr                      Ile

GlyValArgThrIleThrThrGlyAlaProIleThrTyrSerThrTyrArgLysPheLeu
C200     3841    GGGGTAAGGACCATCACCACAGGTGCCCCCATTACGTACTCCACCTATCGCAAGTTCCTT
HCV-1            -----G--A--A--T-----T--CAG------C--------------CG-----------
                                         Ser                              Gly

AlaAspGlyGlyCysSerGlyGlyAlaTyrAspIleIle
C200     3901    GCCGACGGTGGTTGCTCCGGGGGCGCCTATGACATCATAA 3940
HCV-1            --------C--G-----G--------T--------A----TTTGTGACGAGTGCCACTCC
                                                         IleCysAspGluCysHisSer

HCV-1    3961    ACGGATGCCACATCCATCTTGGGCATCGGCACTGTCCTTGACCAAGCAGAGACTGCGGGG
                 ThrAspAlaThrSerIleLeuGlyIleGlyThrValLeuAspGlnAlaGluThrAlaGly

HCV-1    4021    GCGAGACTGGTTGTGCTCGCCACCGCCACCCCTCCGGGCTCCGTCACTGTGCCCCATCCC
                 AlaArgLeuValValLeuAlaThrAlaThrProProGlySerValThrValProHisPro

SerIle
C200                                                               4134 AAGCATC
HCV-1    4081    AACATCGAGGAGGTTGCTCTGTCCACCACCGGAGAGATCCCTTTTTACGGCAAGGCT---
                 AsnIleGluGluValAlaLeuSerThrThrGlyGluIleProPheTyrGlyLysAla

ProIleGluAlaIleLysGlyGlyArgHisLeuIlePheCysHisSerLysLysLysCys
C200     4141    CCCATCGAGGCCATCAAGGGGGGAAGGCATCTCATCTTCTGCCATTCCAAGAAGAAGTGT
HCV-1            ---C----A-TA-----------G--A---------------T-----A-----------C
                     Val

AspGluLeuAlaAlaLysLeuSerAlaLeuGlyLeuAsnAlaValAlaTyrTyrArgGly
C200     4201    GACGAGCTCGCCGCAAAGCTGTCAGCCCTCGGACTCAATGCCGTGGCGTATTACCGCGGT
HCV-1            -----A--------------GTC--AT-G--CA--------------C--C---------
                                      Val      Ile

LeuAspValSerValIleProThrSerGlyAspValValValValAlaThrAsp
C200     4261    CTTGATGTGTCCGTCATACCAACTAGCGGAGACGTCGTTGTCGTGGCAACAGACGC 4316
HCV-1            -----C----------C--G--C-----C--T--T--C-----------C--T--CCTC

HCV-1    4321    ATGACCGGCTATACCGGCGACTTCGACTCGGTGATAGACTGCAATACGTGTGTCACCCAG
                 MetThrGlyTyrThrGlyAspPheAspSerValIleAspCysAsnThrCysValThrGln

HCV-1    4381    ACAGTCGATTTCAGCCTTGACCCTACCTTCACCATTGAGACAATCACGCTCCCCCAGGAT
                 ThrValAspPheSerLeuAspProThrPheThrIleGluThrIleThrLeuProGlnAsp

HCV-1    4441    GCTGTCTCCCGCACTCAACGTCGGGGCAGGACTGGCAGGGGAAGCCAGGCATCTACAGA
                 AlaValSerArgThrGlnArgArgGlyArgThrGlyArgGlyLysProGlyIleTyrArg
```

FIG. 16A

```
HCV-1  4501  TTTGTGGCACCGGGGGAGCGCCCCTCCGGCATGTTCGACTCGTCCGTCCTCTGTGAGTGC
              PheValAlaProGlyGluArgProSerGlyMetPheAspSerSerValLeuCysGluCys

HCV-1  4561  TATGACGCAGGCTGTGCTTGGTATGAGCTCACGCCCGCCGAGACTACAGTTAGGCTACGA
              TyrAspAlaGlyCysAlaTrpTyrGluLeuThrProAlaGluThrThrValArgLeuArg

HCV-1  4621  GCGTACATGAACACCCCGGGGCTTCCCGTGTGCCAGGACCATCTTGAATTTTGGGAGGGC
              AlaTyrMetAsnThrProGlyLeuProValCysGlnAspHisLeuGluPheTrpGluGly

HCV-1  4681  GTCTTTACAGGCCTCACTCATATAGATGCCCACTTTCTATCCCAGACAAAGCAGAGTGGG
              ValPheThrGlyLeuThrHisIleAspAlaHisPheLeuSerGlnThrLysGlnSerGly

HCV-1  4741  GAGAACCTTCCTTACCTGGTAGCGTACCAAGCCACCGTGTGCGCTAGGGCTCAAGCCCCT
              GluAsnLeuProTyrLeuValAlaTyrGlnAlaThrValCysAlaArgAlaGlnAlaPro

HCV-1  4801  CCCCCATCGTGGGACCAGATGTGGAAGTGTTTGATTCGCCTCAAGCCCACCCTCCATGGG
              ProProSerTrpAspGlnMetTrpLysCysLeuIleArgLeuLysProThrLeuHisGly

HCV-1  4861  CCAACACCCCTGCTATACAGACTGGGCGCTGTTCAGAATGAAATCACCCTGACGCACCCA
              ProThrProLeuLeuTyrArgLeuGlyAlaValGlnAsnGluIleThrLeuThrHisPro

HCV-1  4921  GTCACCAAATACATCATGACATGCATGTCGGCCGACCTGGAGGTCGTCACGAGCACCTGG
              ValThrLysTyrIleMetThrCysMetSerAlaAspLeuGluValValThrSerThrTrp

HCV-1  4981  GTGCTCGTTGGCGGCGTCCTGGCTGCTTTGGCCGCGTATTGCCTGTCAACAGGCTGCGTG
              ValLeuValGlyGlyValLeuAlaAlaLeuAlaAlaTyrCysLeuSerThrGlyCysVal

GluVal
C200                                                          5094 GAAGTC
HCV-1  5041  GTCATAGTGGGCAGGGTCGTCTTGTCCGGGAAGCCGGCAATCATACCTGACAGG------
              ValIleValGlyArgValValLeuSerGlyLysProAlaIleIleProAspArg

LeuTyrArgGluPheAspGluMetGluGluCysAlaSerHisLeuProTyrIleGluGln
C200  5101   CTCTACCGAGAGTTCGATGAGATGGAAGAGTGCGCCTCACACCTCCCCTACATCGAACAG
HCV-1        ---------------------------------T-TCAG---T-A--G--------G--A
                                                SerGln

GlyMetGlnLeuAlaGluGlnPheLysGlnLysAlaLeuGlyLeuLeuGlnThrAlaThr
C200  5161   GGAATGCAGCTCGCCGAGCAATTCAAGCAGAAGGCGCTCGGGTTGCTGCAAACAGCCACC
HCV-1        --G----AT------------G---------------C-----CC-C-----G--C--GT--
                Met                                                   Ser

LysGlnAlaGluAlaAlaAlaProCysGluSerMetHisAlaSer
C200  5221   AAGCAAGCGGAGGCTGCTGCTCCGTGTGAGTCAATGCACGCCTCGA
HCV-1        CGT---G---A----T-ATC---C--TGC--TCCAG--CCA--TGGCAA-AACTCGAGACCTTC
              Arg         ValIle         AlaValGlnThrAsnTrpGlnLysLeuGluThrPhe

HCV-1  5281  TGGGCGAAGCATATGTGGAACTTCATCAGTGGGATACAATA
              TrpAlaLysHisMetTrpAsnPheIleSerGlyIleGln
```

FIG. 16B

```
J1   1     GTCTAGCCATGGCGTTAGTATGAGTGTCGTGCAGCCTCCAGGACCCCCCCCCCC
HCV-1      -----------------------------------------------------

J1         GGGAGAGCCATAGTGGTCTGCGGAACCGGTGAGTACACCGGAATTGCCAGGACGACCGGG
HCV-1      ------------------------------------------------------------

J1         TCCTTTCTTGGATCAACCCGCTCAATGCCTGGAGATTTGGCGTGCCCCCGCGAGACTGC
HCV-1      -------------------------------------------------A--------

J1         TAGCCGAGTAGTGTTGGGTCGCGAAAGGCCTTGTGGTACTGCCTGATAGGGTGCTTGCGA
HCV-1      ------------------------------------------------------------

MetSerThrAsnProLysProGlnArgLys
J1         GTGCCCCGGGAGGTCTCGTAGACCGTGCATCATGAGCACAAATCCTAAACCTCAAAGAAA
HCV-1      ------------------------------C---------G-----------------A---
                                                                       Lys

ThrLysArgAsnThrAsnArgArgProGlnAspValLysPheProGlyGlyGlyGlnIle
J1         AACCAAACGTAACACCAACCGCCGCCCACAGGACGTCAAGTTCCCGGGCGGTGGTCAGAT
HCV-1      --A-----------------T--------------------------T--C---------
             Asn

ValGlyGlyValTyrLeuLeuProArgArgGlyProArgLeuGlyValArgAlaThrArg
J1         CGTTGGTGGAGTTTACCTGTTGCCGCGCAGGGGCCCCAGGTTGGGTGTGCGCGCGACTAG
HCV-1      ----------------T-----------------T--A-------------------G--

LysThrSerGluArgSerGlnProArgGlyArgArgGlnProIleProLysAlaArgGln
J1         GAAGACTTCCGAGCGGTCGCAACCTCGTGGAAGGCGACAACCTATCCCCAAGGCTCGCCA
HCV-1      A---------------------------A--T--A--T--G----------------T-G
                                                                     Arg

ProGluGlyArgAlaTrpAlaGlnProGlyTyrProTrpProLeuTyrGlyAsnGluGly
J1         GCCCGAGGGCAGGGCCTGGGCTCAGCCCGGGTACCCTTGGCCCCTCTATGGCAACGAGGG
HCV-1      -------------A----------------------------------------T-----
                       Thr

MetGlyTrpAlaGlyTrpLeu
J1         CATGGGGTGGGCAGGATGGCTCC
HCV-1      -TGC--------G----------
            Cys
```

FIG. 18

```
# 1:  ssc200c-eh1.3.tx   777      98.07%
# 2:  ssc200c-eh1.4.ax   777      98.07%
# 3:  ssc200c-eh1.6.ax   778      97.94%

0  ggta. [CCTTGAATTCTCGTCTT] g [TCCGGGAAGCCGGCAATCATTCCCGATAGGG
    0  ggtac [CCTTGAATTCTCGTCTT] . [TCCGGGAAGCCGGCAATCATTCCCGATAGGG
    0  ggta. [CCTTGAATTCTCGTCTT] g [TCCGGGAAGCCGGCAATCATTCCCGATAGGG 53  AAGTCCTCTACCGAGAGTTCG] a [TGAGATGGAAGAGTGCGCCTCACACCTCCCCTAC
   53  AAGTCCTCTACCGAGAGTTCG] a [TGAGATGGAAGAGTGCGCCTCACACCTCCCCTAC
   53  AAGTCCTCTACCGAGAGTTCG] g [TGAGATGGAAGAGTGCGCCTCACACCTCCCCTAC 109  ATCGAACAGGGAATGCAGCTCGCCGAGCA] a [TTCAAGCAGAA] g [GCGCTCGGGT
  109  ATCGAACAGGGAATGCAGCTCGCCGAGCA] g [TTCAAGCAGAA] g [GCGCTCGGGT
  109  ATCGAACAGGGAATGCAGCTCGCCGAGCA] a [TTCAAGCAGAA] a [GCGCTCGGGT 161  TGCTGCAAACAGCCACCAAGCAAGCGGAGGCTGCTGCTCCCGTGGTGGAGTCCAAATGGC
  161  TGCTGCAAACAGCCACCAAGCAAGCGGAGGCTGCTGCTCCCGTGGTGGAGTCCAAATGGC
  161  TGCTGCAAACAGCCACCAAGCAAGCGGAGGCTGCTGCTCCCGTGGTGGAGTCCAAATGGC 221  ] g [CGCCCTCGAGGCCTTCTGGGCGAAGCACATGTGGAA] t [TTCATCAGCGGGAT
  221  ] a [CGCCCTCGAGGCCTTCTGGGCGAAGCACATGTGGAA] c [TTCATCAGCGGGAT
  221  ] a [CGCCCTCGAGGCCTTCTGGGCGAAGCACATGTGGAA] c [TTCATCAGCGGGAT 273  ACAGTACCTAGCAGGCTTGTCCACTCTGCCTGGAAACCCCGCGATAGCATCATTGATGGC
  273  ACAGTACCTAGCAGGCTTGTCCACTCTGCCTGGAAACCCCGCGATAGCATCATTGATGGC
  273  ACAGTACCTAGCAGGCTTGTCCACTCTGCCTGGAAACCCCGCGATAGCATCATTGATGGC 333  ATTCACAGCCTCTATCACCAGCCCGCTCACCACTCAAAGTACCCTCCTGTTTAACATCTT
  333  ATTCACAGCCTCTATCACCAGCCCGCTCACCACTCAAAGTACCCTCCTGTTTAACATCTT
  333  ATTCACAGCCTCTATCACCAGCCCGCTCACCACTCAAAGTACCCTCCTGTTTAACATCTT
```

FIG.19A

```
393  GGGGGGATGGGTGGCTGCCCAACTCGCCCCTCCCAGCGCTGCCTCGGCTTTTGTGGGCGC
393  GGGGGGATGGGTGGCTGCCCAACTCGCCCCTCCCAGCGCTGCCTCGGCTTTTGTGGGCGC
393  GGGGGGATGGGTGGCTGCCCAACTCGCCCCTCCCAGCGCTGCCTCGGCTTTTGTGGGCGC

453  CGGCATTGCCGGTGCGGCTGTTGGCAGCATAGGCCTC] g [GGAAGGTGCTTGTGGACA
453  CGGCATTGCCGGTGCGGCTGTTGGCAGCATAGGCCTC] a [GGAAGGTGCTTGTGGACA
453  CGGCATTGCCGGTGCGGCTGTTGGCAGCATAGGCCTC] g [GGAAGGTGCTTGTGGACA

509  TCCTGGCGGGATATGG] g [GCAGGAGTGGCTGGCGCTCTCGTGGCCTTTAAGGTCATG
509  TCCTGGCGGGATATGG] g [GCAGGAGTGGCTGGCGCTCTCGTGGCCTTTAAGGTCATG
509  TCCTGGCGGGATATGG] g [GCAGGAGTGGCTGGCGCTCTCGTGGCCTTTAAGGTCATG

565  AGCGGCGAGATGCCCTCCGCTGAGGACATGGTCAACTTACTCCCTGCCATCCTCTCTCCT
565  AGCGGCGAGATGCCCTCCGCTGAGGACATGGTCAACTTACTCCCTGCCATCCTCTCTCCT
565  AGCGGCGAGATGCCCTCCGCTGAGGACATGGTCAACTTACTCCCTGCCATCCTCTCTCCT

625  GGCGCCCTGGTTGTC] g [GGGTTGTGTGCGCAGCAGTACTGCGCCGGCACGTGGGCCC
625  GGCGCCCTGGTTGTC] a [GGGTTGTGTGCGCAGCAGTACTGCGCCGGCACGTGGGCCC
625  GGCGCCCTGGTTGTC] g [GGGTTGTGTGCGCAGCAGTACTGCGCCGGCACGTGGCCCC

681  GGG] a [GAGGGGGCTGTGCAGTGGATGAACCGGCTGATAGCGTTCGCTTCGCGGGGCA
681  GGG] g [GAGGGGGCTGTGCAGTGGATGAACCGGCTGATAGCGTTCGCTTCGCGGGGCA
681  GGG] a [GAGGGGGCTGTGCAGTGGATGAACCGGCTGATAGCGTTCGCTTCGCGGGGCA

737  A] c [CATGTTTCCCCCACGCACTAC] . [GGGATCGATCCTCTAGA]
737  A] t [CATGTTTCCCCCACGCACTAC] . [GGGATCGATCCTCTAGA]
737  A] c [CATGTTTCCCCCACGCACTAC] g [GGGATCGATCCTCTAGA]
```

FIG. 19B

HEPATITIS C VIRUS ISOLATE POLYPEPTIDES

CROSS-REFERENCE TO RELATED APPLICATION

This application is a divisional application of U.S. Ser. No. 08/201,066 filed Feb. 24, 1994, now U.S. Pat. No. 5,372,928, which is a continuation application of U.S. Ser. No. 08/101,280, filed Aug. 2, 1993, now abandoned, which is a continuation application of U.S. Ser. No. 07/637,380, filed Jan. 4, 1991, now abandoned, which is a continuation-in-part application of U.S. Ser. No. 07/456,142, filed Dec. 21, 1989, now abandoned, which is a continuation-in-part application of U.S. Ser. No. 07/408,045, filed Sep. 15, 1989, now abandoned.

TECHNICAL FIELD

The present invention relates to new isolates of the viral class Hepatitis C, polypeptides, polynucleotides and antibodies derived therefrom, as well as the use of such polypeptides, polynucleotides and antibodies in assays (e.g., immunoassays, nucleic acid hybridization assays, etc.) and in the production of viral polypeptides.

BACKGROUND

Non-A, Non-B hepatitis (NANBH) is a transmissible disease or family of diseases that are believed to be viral-induced, and that are distinguishable from other forms of viral-associated liver diseases, including that caused by the known hepatitis viruses, i.e., hepatitis A virus (HAV), hepatitis B virus (HBV), and delta hepatitis virus (HDV), as well as the hepatitis induced by cytomegalovirus (CMV) or Epstein-Barr virus (EBV). NANBH was first identified in transfused individuals. Transmission from man to chimpanzee and serial passage in chimpanzees provided evidence that NANBH is due to a transmissible infectious agent or agents. Epidemiologic evidence is suggestive that there may be three types of NANBH: the water-borne epidemic type; the blood or needle associated type; and the sporadically occurring (community acquired) type. However, until recently, no transmissible agent responsible for NANBH had not been identified.

Clinical diagnosis and identification of NANBH has been accomplished primarily by exclusion of other viral markers. Among the methods used to detect putative NANBH antigens and antibodies are agar-gel diffusion, counterimmunoelectrophoresis, immunofluorescence microscopy, immune electron microscopy, radioimmunoassay, and enzyme-linked immunosorbent assay. However, none of these assays has proved to be sufficiently sensitive, specific, and reproducible to be used as a diagnostic test for NANBH.

Until recently there has been neither clarity nor agreement as to the identity or specificity of the antigen antibody systems associated with agents of NANBH. It is possible that NANBH is caused by more than one infectious agent and unclear what the serological assays detect in the serum of patients with NANBH.

In the past, a number of candidate NANBH agents were postulated. See, e.g., Prince (1983) Ann. Rev. Microbiol. 37:217; Feinstone & Hoofnagle (1984) New Eng. J. Med. 311:185; Overby (1985) Curr. Heptol. 5:49; Overby (1986) Curr. Heptol. 6:65; Overby (1987) Curr. Heptol. 7:35; and Iwarson (1987) British Med. J. 295:946. However, there is no proof that any of these candidates represent the etiological agent of NANBH.

In 1987, Houghton et al. cloned the first virus definitively linked to NANBH. See, e.g., EPO Pub. Nos. 318,216 and 388 232; Houghton et al., Science 244:359 (1989). Houghton et al. described therein the cloning of an isolate from a new viral class, hepatitis C virus (HCV), the prototype isolate described therein being named "HCV1". HCV is a Flavi-like virus, with an RNA genome. Houghton et al. described the production of recombinant proteins from HCV sequences that are useful as diagnostic reagents, as well as polynucleotides useful in diagnostic hybridization assays and in the cloning of additional HCV isolates.

The demand for sensitive, specific methods for screening and identifying carriers of NANBH and NANBH contaminated blood or blood products is significant. Post-transfusion hepatitis (PTH) occurs in approximately 10% of transfused patients, and NANBH accounts for up to 90% of these cases. There is a frequent progression to chronic liver damage (25–55%).

Patient care as well as the prevention of transmission of NANBH by blood and blood products or by close personal contact require reliable diagnostic and prognostic tools to detect nucleic acids, antigens and antibodies related to NANBH. In addition, there is also a need for effective vaccines and immunotherapeutic therapeutic agents for the prevention and/or treatment of the disease.

While at least one HCV isolate has been identified which is useful in meeting the above needs, additional isolates, particularly those with divergent a genome, may prove to have unique applications.

SUMMARY OF THE INVENTION

New isolates of HCV have been characterized from Japanese blood donors who have been implicated as NANBH carriers. These isolates exhibit nucleotide and amino acid sequence heterogeneity with respect to the prototype isolate, HCV1, in several viral domains. It is believed that these distinct sequences are of importance, particularly in diagnostic assays and in vaccine development.

In one embodiment, the present invention provides a DNA molecule comprising a nucleotide sequence of at least 15 bp from an HCV isolate substantially homologous to an isolate selected from the group J1 or J7, wherein said nucleotide sequence is distinct from the nucleotide sequence of HCV isolate HCV1.

In another embodiment, the present invention provides a DNA molecule comprising a nucleotide sequence of at least 15 bp encoding an amino acid sequence from a HCV isolate J1 or J7 wherein the J1 or J7 amino acid sequence is distinct from the amino acid sequence of HCV isolate HCV1.

Yet another embodiment of the present invention provides a purified polypeptide comprising an amino acid sequence from an HCV isolate substantially homologous to an isolate selected from the group J1 and J7, wherein said amino acid sequence is distinct from the sequence of the polypeptides encoded by the HCV isolate HCV1.

Still another embodiment of the present invention provides a polypeptide comprising an amino acid sequence from a HCV isolate J1 or J7 wherein the J1 or J7 amino acid sequence is distinct from the amino acid sequence of HCV isolate HCV1 and the polypeptide is immobilized on a solid support.

In a further embodiment of the present invention, an immunoassay for detecting the presence of anti-HCV antibodies in a test sample is provided comprising: (a) incubating the test sample under conditions that allow the formation of antigen-antibody complexes with an immunogenic polypeptide comprising an amino acid sequence from an HCV isolate substantially homologous to an isolate selected from the group J1 and J7, wherein the amino acid sequence is distinct from the amino acid sequence of HCV isolate HCV1; and (b) detecting an antigen-antibody complex comprising the immunogenic polypeptide.

The present invention also provides a composition comprising anti-HCV antibodies that bind an HCV epitope substantially free of antibodies that do not bind an HCV epitope, wherein: (a) the HCV epitope comprises an amino acid sequence from an HCV isolate substantially homologous to an isolate selected from the group J1 and J7, wherein the amino acid sequence is distinct from the amino acid sequence of HCV isolate HCV1; and (b) the J1 or J7 amino acid sequence is not immunologically cross-reactive with HCV1.

A further embodiment of the present invention provides an immunoassay for detecting the presence of an HCV polypeptide in a test sample comprising: (a) incubating the test sample under conditions that allow the formation of antigen-antibody complexes with anti-HCV antibodies that bind an HCV epitope wherein: (i) the HCV epitope comprises an amino acid sequence from a HCV isolate J1 or J7; (ii) the J1 or J7 amino acid sequence is distinct from the amino acid sequence of HCV isolate HCV1; and (iii) the J1 or J7 amino acid sequence is not immunologically cross-reactive with HCV1; and (b) detecting an antigen-antibody complex comprising the anti-HCV antibodies.

Also provided by the present invention is a method of producing anti-HCV antibodies comprising administering to a mammal a polypeptide comprising an amino acid sequence from a HCV isolate J1 or J7 wherein the J1 or J7 amino acid sequence is distinct from the amino acid sequence of HCV isolate HCV1 whereby the mammal produces anti-HCV antibodies.

Yet another embodiment of the present invention provides a method of detecting HCV polynucleotides in a test sample comprising: (a) providing a probe comprising the DNA molecule of claim 1; (b) contacting the test sample and the probe under conditions that allow for the formation of a polynucleotide duplex between the probe and its complement in the absence of substantial polynucleotide duplex formation between the probe and non-HCV polynucleotide sequences present in the test sample; and (c) detecting any polynucleotide duplexes comprising the probe.

A still further embodiment of the present invention provides a method of producing a recombinant polypeptide comprising an HCV amino acid sequence, the method comprising: (a) providing host cells transformed by a DNA construct comprising a control sequences for the host cell operably linked to a coding sequence encoding an amino acid sequence from a HCV isolate J1 or J7 wherein the J1 or J7 amino acid sequence is distinct from the amino acid sequence of HCV isolate HCV1; (b) growing the host cells under conditions whereby the coding sequence transcribed and translated into the recombinant polypeptide; and (c) recovering the recombinant polypeptide.

These and other embodiments of the present invention will be readily apparent to those of ordinary skill in the art in view of the following description.

BRIEF DESCRIPTION OF THE FIGURES

FIG. 1 shows the consensus sequence of the coding strand of a fragment from the J7 C/E domain with the heterogeneities.

FIG. 2 shows the consensus sequence of the coding strand of a fragment from the J1 E domain with the heterogeneities.

FIG. 3 shows the consensus sequence of the coding strand of a fragment of the J1 E/NS1 domain with the heterogeneities.

FIG. 4 shows the consensus sequence of the coding strand of a fragment from the J1 NS3 domain with the heterogeneities.

FIG. 5 shows the consensus sequence of the coding strand of a fragment from the J1 NS5 domain with the heterogeneities.

FIG. 6 shows the homology of the J7 C/E consensus sequence with the nucleotide sequence of the same domain from HCV1.

FIG. 7 shows the homology of the J1 E consensus sequence with the nucleotide sequence of the same domain from HCV1.

FIG. 8 shows the homology of the J1 E/NS1 consensus sequence with the nucleotide sequence of the same domain from HCV1.

FIG. 9 shows the homology of the J1 NS3 consensus sequence with the nucleotide sequence of the same domain from HCV1.

FIG. 10 shows the homology of the J1 NS5 consensus sequence with the nucleotide sequence of the same domain from HCV1.

FIG. 12 shows the nucleotide sequence of the ORF of HCV1.

FIG. 13 shows the consensus sequence of the coding strand of a fragment from the J1 NS1 domain (J1 1519) with the nucleotide sequence of the same domain from HCV1. Also shown are the amino acids encoded therein.

FIG. 14 shows a composite of the consensus sequence from the core to the NS1 domain of J1 with the nucleotide sequence of the same domain from HCV1. Also shown are the amino acids encoded therein.

FIG. 15 shows a consensus sequence of the coding strand of the NS1 domain of J1, as determined in Example IV.B. and .C. Also shown are the amino acids encoded therein.

FIG. 16 shows a consensus sequence of a coding strand of the C200 region of the NS3–NS4 domain of J1, as determined in Example IV.A., .D., and .E. Also shown are the nucleotide sequence of the same domain from HCV1. Also shown are the amino acids encoded in the sequences.

FIG. 17 shows a consensus sequence of the coding strand of the NS1 domain of J1, as determined in Example V. Also shown are the nucleotide sequence of the same domain from HCV1, and the amino acids encoded in the sequences.

FIG. 18 shows a consensus sequence of the coding strand of the untranslated and core domains of J1, as determined in Example VI. Also shown are the nucleotide sequence of the same domain from HCV1, and the amino acids encoded in the sequences.

FIG. 19 shows a comparison of three different clones of the NS3–NS4 domain of J1, as determined in Example IV.E.

DETAILED DESCRIPTION OF THE INVENTION

Figure 11:
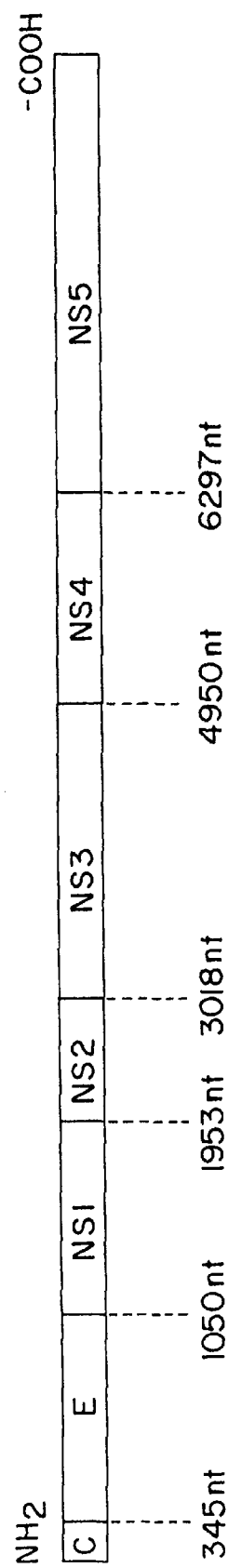
FIG. 11 shows the putative genomic organization of the HCV1 genome.

The practice of the present invention will employ, unless otherwise indicated, conventional techniques of molecular biology, microbiology, recombinant DNA techniques, and immunology, which are within the skill of the art. Such techniques are explained fully in the literature. See e.g., Sambrook, et al., MOLECULAR CLONING; A LABORATORY MANUAL (1989); DNA CLONING, VOLUMES I AND II (D. N. Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, New York), and HANDBOOK OF EXPERIMENTAL IMMUNOLOGY, VOLUMES I–IV (D. M. Weir and C. C. Blackwell eds 1986). All patents, patent applications, and other publications mentioned herein, both supra and infra, are hereby incorporated herein by reference.

The term "hepatitis C virus" has been reserved by workers in the field for an heretofore unknown etiologic agent of NANBH. Accordingly, as used herein, "hepatitis C virus" (HCV) refers to an agent causative of NANBH, which was formerly referred to as NANBV and/or BB-NANBV from the class of the prototype isolate, HCV1, described by Houghton et al. See, e.g., EPO Pub. Nos. 318,216 and 388,232. The nucleotide sequence and putative amino acid sequence of HCV1 is shown in FIG. 6. The terms HCV, NANBV, and BB-NANBV are used interchangeably herein. As an extension of this terminology, the disease caused by HCV, formerly called NANB hepatitis (NANBH), is called hepatitis C. The terms NANBH and hepatitis C are used interchangeably herein. The term "HCV", as used herein, denotes a viral species of which pathogenic strains cause NANBH, as well as attenuated strains or defective interfering particles derived therefrom.

HCV is a Flavi-like virus. The morphology and composition of Flavivirus particles are known, and are discussed by Brinton (1986) THE VIRUSES: THE TOGAVIRIDAE AND FLAVIVIRIDAE (Series eds. Fraenkel-Conrat and Wagner, vol eds. Schlesinger and Schlesinger, Plenum Press), p.327–374. It has recently been found that portions of the HCV genome are also homologous to pestiviruses. Generally, with respect to morphology, Flaviviruses contain a central nucleocapsid surrounded by a lipid bilayer. Virions are spherical and have a diameter of, about 40–50 nm. Their cores are about 25–30 nm in diameter. Along the outer surface of the virion envelope are projections that are about 5–10 nm long with terminal knobs about 2 nm in diameter.

The HCV genome is comprised of RNA. It is known that RNA containing viruses have relatively high rates of spontaneous mutation, i.e., reportedly on the order of $10^{-3}$ to $10^{-4}$ per incorporated nucleotide. Therefore, there are multiple strains, which may be virulent or avirulent, within the HCV class or species.

It is believed that the genome of HCV isolates is comprised of a single ORF of approximately 9,000 nucleotides to approximately 12,000 nucleotides, encoding a polyprotein similar in size to that of HCV1, an encoded polyprotein of similar hydrophobic and antigenic character to that of HCV1, and the presence of co-linear peptide sequences that are conserved with HCV1. In addition, the genome is believed to be a positive-stranded RNA.

Isolates of HCV comprise epitopes that are immunologically cross-reactive with epitopes in the HCV1 genome. At least some of these are epitopes unique to HCV when compared to other known Flaviviruses. The uniqueness of the epitope may be determined by its immunological reactivity with anti-HCV antibodies and lack of immunological reactivity with antibodies to other Flavivirus species. Methods for determining immunological reactivity are known in the art, for example, by radioimmunoassay, by ELISA assay, by hemagglutination, and several examples of suitable techniques for assays are provided herein.

It is also expected that the overall homology of HCV isolates and HCV1 genomes at the nucleotide level probably will be about 40% or greater, probably about 60% or greater, and even more probably about 80% to about 90% or greater. In addition that there are many corresponding contiguous sequences of at least about 13 nucleotides that are fully homologous. The correspondence between the sequence from a new isolate and the HCV1 sequence can be determined by techniques known in the art. For example, they can be determined by a direct comparison of the sequence information of the polynucleotide from the new isolate and HCV1 sequences. Alternatively, homology can be determined by hybridization of the polynucleotides under conditions which form stable duplexes between homologous regions (for example, those which would be used prior to $S_1$ digestion), followed by digestion with single-stranded specific nuclease(s), followed by size determination of the digested fragments.

Because of the evolutionary relationship of the strains or isolates of HCV, putative HCV strains or isolates are identifiable by their homology at the polypeptide level. Thus, new HCV isolates are expected to be more than about 40% homologous, probably more than about 70% homologous, and even more probably more than about 80% homologous, and possibly even more than about 90% homologous at the polypeptide level. The techniques for determining amino acid sequence homology are known in the art. For example, the amino acid sequence may be determined directly and compared to the sequences provided herein. Alternatively the nucleotide sequence of the genomic material of the putative HCV may be determined, the amino acid sequence encoded therein can be determined, and the corresponding regions compared.

The ORF of HCV1 is shown in FIG. 12. The non-structural, core, and envelope domains of the polyprotein have been predicted for HCV1 (FIG. 11). The "C", or core, polypeptide is believed to begin at the amino terminus of the large ORF and to continue until about amino acid 115 of HCV1. The putative "E", or envelope, domain of HCV1 is believed to begin at about amino acid 116 to about amino acid 350. Putative NS1, or non-structural one domain, is thought to begin at about 350 to about amino acid 651. For the remaining domains, putative NS2 is thought to begin at about amino acid 652 to about amino acid 1006, putative NS3 from about amino acid 1007 to about amino acid 1650, putative NS4 from about amino acid 1651 to about amino acid 2099, and putative NS5 from about amino acid 2300 to the carboxy terminus of the large ORF. The above boundaries are approximations based on an analysis of the ORF. The exact boundaries can be determined by those skilled in the art in view of the disclosure herein. "HCV/J1" or "J1" and "HCV/J7" or "J7" refer to new HCV isolates characterized by the nucleotide sequence disclosed herein, as well as related isolates that are substantially homologous thereto;

i.e., at least about 90% or about 95% at the nucleotide level. It is believed that the sequences disclosed herein characterize an HCV subclass that is predominant in Japan and other Asian and/or Pacific rim countries. Additional J1 and J7 isolates can be obtained in view of the disclosure herein and EPO Pub. Nos. 318,216 and 388,232. In particular, the J1 and J7 nucleotide sequences disclosed herein, as well as the HCV1 sequences in FIG. 12, can be used as primers or probes to clone additional domains of J1, J7, or additional isolates.

As used herein, a nucleotide sequence "from" a designated sequence or source refers to a nucleotide sequence that is homologous (i.e., identical) to or complementary to the designated sequence or source, or a portion thereof. The J1 sequences provided herein are a minimum of about 6 nucleotides, preferably about 8 nucleotides, more preferably about 15 nucleotides, and most preferably 20 nucleotides or longer. The maximum length is the complete viral genome.

The term "substantially homologous" refers to an HCV isolate which is at least 60% identical in sequence to the reference isolate when the entire ORF is compared, where the sequence identity is preferably at least 75%, more preferably at least 80%, still more preferably at least 85%, especially more than about 90%, most preferably 95% or greater, particularly 98% or greater. Thus, for example, a new isolate having genome which is 80% identical to J1 is considered to be substantially homologous to J1.

In some aspects of the invention, the sequence of the region from which the polynucleotide is derived is preferably homologous to or complementary to a sequence which is unique to an HCV genome or the J1 and J7 genome. Whether or not a sequence is unique to a genome can be determined by techniques known to those of skill in the art. For example, the sequence can be compared to sequences in databanks, e.g., Genebank, to determine whether it is present in the uninfected host or other organisms. The sequence can also be compared to the known sequences of other viral agents, including those which are known to induce hepatitis, e.g., HAV, HBV, and HDV, and to other members of the Flaviviridae. The correspondence or non-correspondence of the derived sequence to other sequences can also be determined by hybridization under the appropriate stringency conditions. Hybridization techniques for determining the complementarity of nucleic acid sequences are known in the art. See also, for example, Maniatis et al. (1982) MOLECULAR CLONING; A LABORATORY MANUAL (Cold Spring Harbor Press, Cold Spring Harbor, N.Y.). In addition, mismatches of duplex polynucleotides formed by hybridization can be determined by known techniques, including for example, digestion with a nuclease such as S1 that specifically digests single-stranded areas in duplex polynucleotides. Regions from which typical DNA sequences may be derived include, but are not limited to, regions encoding specific epitopes, as well as non-transcribed and/or non-translated regions.

The J1 of J7 polynucleotide is not necessarily physically derived from the nucleotide sequence shown, but may be generated in any manner, including for example, chemical synthesis or DNA replication or reverse transcription or transcription. In addition, combinations of regions corresponding to that of the designated sequence may be modified in ways known in the art to be consistent with an intended use. The polynucleotides may also include one or more labels, which are known to those of skill in the art.

An amino acid sequence "from" a designated polypeptide or source of polypeptides means that the amino acid sequence is homologous (i.e., identical) to the sequence of the designated polypeptide, or a portion thereof. An amino acid sequence "from" a designated nucleic acid sequence refers to a polypeptide having an amino acid sequence identical to that of a polypeptide encoded in the sequence, or a portion thereof. The J1 or J7 amino acid sequences in the polypeptides of the present invention are at least about 5 amino acids in length, preferably at least about 10 amino acids, more preferably at least about 15 amino acids, and most preferably at least about 20 amino acids.

The polypeptides of the present invention are not necessarily translated from a designated nucleic acid sequence; the polypeptides may be generated in any manner, including for example, chemical synthesis, or expression of a recombinant expression system, or isolation from virus. The polypeptides may include one or more analogs of amino acids or unnatural amino acids. Methods of inserting analogs of amino acids into a sequence are known in the art. The polypeptides may also include one or more labels, which are known to those of skill in the art.

The term "recombinant polynucleotide" as used herein intends a polynucleotide of genomic, cDNA, semisynthetic, or synthetic origin which, by virtue of its origin or manipulation: (1) is linked to a polynucleotide other than that to which it is linked in nature, or (2) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

The term "purified polypeptide" refers to a polypeptide which is substantially free of other HCV viral components, particularly polynucleotides. A polypeptide composition is "substantially free" of another component if the weight of the polypeptide in the composition is at least 70% of the weight of the polypeptide and other component combined, more preferably at least about 80%, still more preferably about 90%, and most preferably 95% or greater. For example, a composition containing 100 $\mu$g/mL HCV polypeptide and only 3 $\mu$g/mL other HCV components (e.g., DNA, lipids, etc.) is substantially free of "other HCV viral components", and thus is a composition of an isolated polypeptide within the scope of this definition. Similarly, a "purified polynucleotide" is a polynucleotide which is substantially free of other HCV viral components, particularly polypeptides.

"Recombinant host cells", "host cells", "cells", "cell lines", "cell cultures", and other such terms denote microorganisms or higher eukaryotic cell lines cultured as unicellular entities that can be, or have been, used as recipients for a recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation.

A "replicon" is any genetic element, e.g., a plasmid, a chromosome, a virus, a cosmid, etc. that behaves as an autonomous unit of polynucleotide replication within a cell; i.e., capable of replication under its own control.

A "cloning vector" is a replicon that can transform a selected host cell and in which another polynucleotide segment is attached, so as to bring about the replication and/or expression of the attached segment. Typically, cloning vectors include plasmids, virus (e.g., bacteriophage vector) and cosmids.

An "integrating vector" is a vector that does not behave as a replicon in a selected host cell, but has the ability to integrate into a replicon (typically a chromosome) resident in the selected host to stably transform the host.

An "expression vector" is a construct that can transform a selected host cell and provides for expression of a heterologous coding sequence in the selected host. Expression vectors can be either cloning vectors or integrating vectors.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, and recombinant polynucleotide sequences.

"Control sequence" refers to polynucleotide regulatory sequences which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers. The term "control sequences" is intended to include, at a minimum, all components the presence of which are necessary for expression, and may also include additional advantageous components.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" or ORF is a region of a polynucleotide sequence which encodes a polypeptide; this region may represent a portion of a coding sequence or a total coding sequence.

"Immunologically cross-reactive" refers to two or more epitopes or polypeptides that are bound by the same antibody. Cross-reactivity can be determined by any of a number of immunoassay techniques, such as a competition assay.

As used herein, the term "antibody" refers to a polypeptide or group of polypeptides which comprise at least one epitope. An "antigen binding site" is formed from the folding of the variable domains of an antibody molecule(s) to form three-dimensional binding sites with an internal surface shape and charge distribution complementary to the features of an epitope of an antigen, which allows specific binding to form an antibody-antigen complex. An antigen binding site may be formed from a heavy- and/or light-chain domain (VH and VL, respectively), which form hypervariable loops which contribute to antigen binding. The term "antibody" includes, without limitation, chimeric antibodies, altered antibodies,univalent antibodies, Fab proteins, and single-domain antibodies. In many cases, the biding phenomena of antibodies to antigens is equivalent to other ligand/anti-ligand binding.

As used herein, a "single domain antibody" (dAb) is an antibody which is comprised of an HL domain, which binds specifically with a designated antigen. A dAb does not contain a VL domain, but may contain other antigen binding domains known to exist to antibodies, for example, the kappa and lambda domains. Methods for preparing dabs are known in the art. See, for example, Ward et al, Nature 341: 544 (1989).

Antibodies may also be comprised of VH and VL domains, as well as other known antigen binding domains. Examples of these types of antibodies and methods for their preparation and known in the art (see, e.g., U.S. Pat. No. 4,816,467, which is incorporated herein by reference), and include the following. For example, "vertebrate antibodies" refers to antibodies which are tetramers or aggregates thereof, comprising light and heavy chains which are usually aggregated in a "Y" configuration and which may or may not have covalent linkages between the chains. In vertebrate antibodies, the amino acid sequences of the chains are homologous with those sequences found in antibodies produced in vertebrates, whether in situ or in vitro (for example, in hybridomas). Vertebrate antibodies include, for example, purified polyclonal antibodies and monoclonal antibodies, methods for the preparation of which are described infra.

"Hybrid antibodies" are antibodies where chains are separately homologous with reference to mammalian antibody chains and represent novel assemblies of them, so that two different antigens are precipitable by the tetramer or aggregate. In hybrid antibodies, one pair of heavy and light chains are homologous to those found in an antibody raised against a first antigen, while a second pair of chains are homologous to those found in an antibody raised against a second antibody. This results in the property of "divalence", i.e., the ability to bind two antigens simultaneously. Such hybrids may also be formed using chimeric chains, as set forth below.

"Chimeric antibodies" refers to antibodies in which the heavy and/or light chains are fusion proteins. Typically, one portion of the amino acid sequences of the chain is homologous to corresponding sequences in an antibody derived from a particular species or a particular class, while the remaining segment of the chain is homologous to the sequences derived from another species and/or class. Usually, the variable region of both light and heavy chains mimics the variable regions or antibodies derived from one species of vertebrates, while the constant portions are homologous to the sequences in the antibodies derived from another species of vertebrates. However, the definition is not limited to this particular example. Also included is any antibody in which either or both of the heavy or light chains are composed of combinations of sequences mimicking the sequences in antibodies of different sources, whether these sources be from differing classes or different species of origin, and whether or not the fusion point is at the variable/constant boundary. Thus, it is possible to produce antibodies in which neither the constant nor the variable region mimic know antibody sequences. It then becomes possible, for example, to construct antibodies whose variable region has a higher specific affinity for a particular antigen, or whose constant region can elicit enhanced complement fixation, or to make other improvements in properties possessed by a particular constant region.

Another example is "altered antibodies", which refers to antibodies in which the naturally occurring amino acid sequence in a vertebrate antibody has been varies. Utilizing recombinant DNA techniques, antibodies can be redesigned to obtain desired characteristics. The possible variations are many, and range from the changing of one or more amino acids to the complete redesign of a region, for example, the constant region. Changes in the constant region, in general, to attain desired cellular process characteristics, e.g., changes in complement fixation, interaction with membranes, and other effector functions. Changes in the variable region may be made to alter antigen binding characteristics. The antibody may also be engineered to aid the specific delivery of a molecule or substance to a specific cell or tissue site. The desired alterations may be made by known techniques in molecular biology, e.g., recombinant techniques, site-directed mutagenesis, etc.

Yet another example are "univalent antibodies", which are aggregates comprised of a heavy-chain/light-chain dimer bound to the Fc (i.e., stem) region of a second heavy chain. This type of antibody escapes antigenic modulation. See, e.g., Glennie et al. Nature 295: 712 (1982). Included also within the definition of antibodies are "Fab" fragments of antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fc portion. "Fab" includes aggregates of one heavy and one light chain (commonly known as Fab'), as well as tetramers containing the 2H and 2L chains (referred to as F(ab)$_2$), which are capable of selectively reacting with a designated antigen or antigen family. Fab antibodies may be divided into subsets analogous to those described above, i.e., "vertebrate Fab", "hybrid Fab", "chimeric Fab", and "altered Fab". Methods of producing Fab fragments of antibodies are known within the art and include, for example, proteolysis, and synthesis by recombinant techniques.

"Epitope" refers to an antibody binding site usually defined by a polypeptide, but also by non-amino acid haptens. An epitope could comprise 3 amino acids in a spatial conformation which is unique to the epitope, generally an epitope consists of at least 5 such amino acids, and more usually, consists of at least 8–10 such amino acids.

"Antigen-antibody complex" refers to the complex formed by an antibody that is specifically bound to an epitope on an antigen.

"Immunogenic polypeptide" refers to a polypeptide that elicits a cellular and/or humoral immune response in a mammal, whether alone or linked to a carrier, in the presence or absence of an adjuvant.

"Polypeptide" refers to a polymer of amino acids and does not refer to a specific length of the molecule. Thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

A "transformed" host cell refers to both the immediate cell that has undergone transformation and its progeny that maintain the originally exogenous polynucleotide.

"Treatment" as used herein refers to prophylaxis and/or therapy.

"Individual", refers to vertebrates, particularly members of the mammalian species, and includes but is not limited to domestic animals, sports animals, and primates, including humans.

"Sense strand" refers to the strand of a double-stranded DNA molecule that is homologous to a mRNA transcript thereof. The "anti-sense strand" contains a sequence which is complementary to that of the "sense strand".

"Antibody-containing body component" refers to a component of an individual's body which is a source of the antibodies of interest. Antibody-containing body components are known in the art, and include but are not limited to, whole blood and components thereof, plasma, serum, spinal fluid, lymph fluid, the external sections of the respiratory, intestinal, and genitourinary tracts, tears, saliva, milk, white blood cells, and myelomas.

"Purified HCV" isolate refers to a preparation of HCV particles which has been isolated from the cellular constituents with which the virus is normally associated, and from other types of viruses which may be present in the infected tissue. The techniques for isolating viruses are known to those of skill in the art, and include, for example, centrifugation and affinity chromatography.

An HCV "particle" is an entire virion, as well as particles which are intermediates in virion formation. HCV particles generally have one or more HCV proteins associated with the HCV nucleic acid.

"Probe" refers to a polynucleotide which forms a hybrid structure with a sequence in a target polynucleotide, due to complementarity of at least one region in the probe with a region in the target.

"Biological sample" refers to a sample of tissue or fluid isolated from an individual, including but not limited to, for example, whole blood and components thereof, plasma, serum, spinal fluid, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

The invention pertains to the isolation and characterization of a newly discovered isolate of HCV, J1 and J7, their nucleotide sequences, their protein sequences and resulting polynucleotides, polypeptides and antibodies derived therefrom. Isolates J1 and J7 are novel in their nucleotide and amino acid sequences, and is believed to characteristic of HCV isolates from Japan and other Asian countries.

The nucleotide sequences derived from HCV/J1 and HCV/J7 are useful as probes to diagnose the presence of virus in samples, and to isolate other naturally occurring variants of the virus. These nucleotide sequences also make available polypeptide sequences of HCV antigens encoded within the J1 and J7 genome and permits the production of polypeptides which are useful as standards or reagents in diagnostic tests and/or as components of vaccines. Antibodies, both polyclonal and monoclonal, directed against HCV epitopes contained within these polypeptide sequences are also useful for diagnostic tests, as therapeutic agents, for screening of antiviral agents, and for the isolation of the NANBH virus. In addition, by utilizing probes derived from the sequences disclosed herein it is possible to isolate and sequence other portions of the J1 and J7 genome, thus giving rise to additional probes and polypeptides which are useful in the diagnosis and/or treatment, both prophylactic and therapeutic, of NANBH.

The availability of the HCV/J1 and HCV/J7 nucleotide sequences enable the construction of polynucleotide probes and polypeptides useful in diagnosing NANBH due to HCV infection and in screening blood donors as well as donated blood and blood products for infection. For example, from the sequences it is possible to synthesize DNA oligomers of about 8–10 nucleotides, or larger, which are useful as hybridization probes to detect the presence of HCV RNA in, for example, sera of subjects suspected of harboring the virus, or for screening donated blood for the presence of the virus. The HCV/J1 and HCV/J7 sequences also allow the design and production of HCV specific polypeptides which are useful as diagnostic reagents for the presence of antibodies raised during NANBH. Antibodies to purified polypeptides derived from the HCV/J1 and HCV/J7 sequences may also be used to detect viral antigens in infected individuals and in blood.

Knowledge of these HCV/J1 and HCV/J7 sequences also enable the design and production of polypeptides which may be used as vaccines against HCV and also for the production of antibodies, which in turn may be used for protection against the disease, and/or for therapy of HCV infected individuals. Moreover, the disclosed HCV/J1 and HCV/J7 sequences enable further characterization of the HCV genome. Polynucleotide probes derived from these sequences, as well as from the HCV genome, may be used to screen cDNA libraries for additional viral cDNA sequences, which, in turn, may be used to obtain additional overlapping sequences. See, e.g., EPO Pub. Nos. 318,216 and 388,232.

The HCV/J1 and HCV/J7 polynucleotide sequences, the polypeptides derived therefrom and the antibodies directed against these polypeptides, are useful in the isolation and identification of the BB-NANBV agent(s). For example, antibodies directed against HCV epitopes contained in polypeptides derived from the HCV/J1 sequences may be used in processes based upon affinity chromatography to isolate the virus. Alternatively, the antibodies may be used to identify viral particles isolated by other techniques. The viral antigens and the genomic material within the isolated viral particles may then be further characterized.

The information obtained from further sequencing of the HCV/J1 and HCV/J7 genome, as well as from further characterization of the HCV/J1 and HCV/J7 antigens and characterization of the genomes enable the design and synthesis of additional probes and polypeptides and antibodies which may be used for diagnosis, for prevention, and for therapy of HCV induced NANBH, and for screening for infected blood and blood-related products.

The availability of HCV/J1 and HCV/J7 cDNA sequences permits the construction of expression vectors encoding antigenically active regions of the polypeptide encoded in either strand. These antigenically active regions may be derived from coat or envelope antigens or from core antigens, or from antigens which are non-structural including, for example, polynucleotide binding proteins, polynucleotide polymerase(s), and other viral proteins required for the replication and/or assembly of the virus particle. Fragments encoding the desired polypeptides are derived from the cDNA clones using conventional restriction digestion or by synthetic methods, and are ligated into vectors which may, for example, contain portions of fusion sequences such as beta-galactosidase or superoxide dismutase (SOD). Methods and vectors which are useful for the production of polypeptides which contain fusion sequences of SOD are described in EPO Pub. No. 196,056. Vectors encoding fusion polypeptides of SOD and HCV polypeptides are described in EPO Pub. No. 318,216. Any desired portion of the HCV cDNA containing an open reading frame, in either sense strand, can be obtained as a recombinant polypeptide, such as a mature or fusion protein. Alternatively, a polypeptide encoded in the cDNA can be provided by chemical synthesis.

The DNA encoding the desired polypeptide, whether in fused or mature form, and whether or not containing a signal sequence to permit secretion, may be ligated into expression vectors suitable for any convenient host. Both eukaryotic and prokaryotic host systems are presently used in forming recombinant polypeptides, and a summary of some of the more common control systems and host cell is given below. The polypeptide produced in such host cells is then isolated from lysed cells or from the culture medium and purified to the extent needed for its intended use. Purification may be by techniques known in the art, for example, differential extraction, salt fractionation, chromatography on ion exchange resins, affinity chromatography, centrifugation, and the like. See, for example, *Methods in Enzymology* for a variety of methods for purifying proteins.

Such recombinant or synthetic HCV polypeptides can be used as diagnostics, or those which give rise to neutralizing antibodies may be formulated into vaccines. Antibodies raised against these polypeptides can also be used as diagnostics, or for passive immunotherapy. In addition, antibodies to these polypeptides are useful for isolating and identifying HCV particles.

The HCV antigens may also be isolated from HCV virions. The virions may be grown in HCV infected cells in tissue culture, or in an infected host.

While the polypeptides of the present invention may comprise a substantially complete viral domain, in many applications all that is required is that the polypeptide comprise an antigenic or immunogenic region of the virus. An antigenic region of a polypeptide is generally relatively small—typically 8 to 10 amino acids or less in length. Fragments of as few as 5 amino acids may characterize an antigenic region. These segments may correspond to regions of HCV/J1 or HCV/J7 epitopes. Accordingly, using the cDNAs of HCV/J1 and HCV/J7 as a basis, DNAs encoding short segments of HCV/J1 and HCV/J7 polypeptides can be expressed recombinantly either as fusion proteins, or as isolated polypeptides. In addition, short amino acid sequences can be conveniently obtained by chemical synthesis.

In instances wherein the synthesized polypeptide is correctly configured so as to provide the correct epitope, but is too small to be immunogenic, the polypeptide may be linked to a suitable carrier. A number of techniques for obtaining such linkage are known in the art, including the formation of disulfide linkages using N-succinimidyl-3-(2-pyridyl-thio) propionate (SPDP) and succinimidyl 4-(N-maleimido-methyl)cyclohexane-1-carboxylate (SMCC) obtained from Pierce Company, Rockford, Ill., (if the peptide lacks a sulfhydryl group, this can be provided by addition of a cysteine residue.) These reagents create a disulfide linkage between themselves and peptide cysteine residues on one protein and an amide linkage through the epsilon-amino on a lysine, or other free amino group in the other. A variety of such disulfide/amide-forming agents are known. See, for example, Immun. Rev. (1982) 62:185. Other bifunctional coupling agents form a thioether rather than a disulfide linkage. Many of these thio-ether-forming agents are commercially available and include reactive esters of 6-maleimidocaproic acid, 2-bromoacetic acid, 2-iodoacetic acid, 4-(N-maleimido-methyl)cyclohexane-1-carboxylic acid, and the like. The carboxyl groups can be activated by combining them with succinimide or 1-hydroxyl-2-nitro-4-sulfonic acid, sodium salt. Additional methods of coupling antigens employs the rotavirus/"binding peptide" system described in EPO Pub. No. 259,149, the disclosure of which is incorporated herein by reference. The foregoing list is not meant to be exhaustive, and modifications of the named compounds can clearly be used.

Any carrier may be used which does not itself induce the production of antibodies harmful to the host. Suitable carriers are typically large, slowly metabolized macromolecules such as proteins; polysaccharides, such as latex functionalized Sepharose®, agarose, cellulose, cellulose beads and the like; polymeric amino acids, such as polyglutamic acid, polylysine, and the like; amino acid copolymers; and inactive virus particles. Especially useful protein substrates are serum albumins, keyhole limpet hemocyanin, immunoglobulin molecules, thyroglobulin, ovalbumin, tetanus toxoid, and other proteins wall known to those skilled in the art.

In addition to full-length viral proteins, polypeptides comprising truncated HCV amino acid sequences encoding at least one viral epitope are useful immunological reagents. For example, polypeptides comprising such truncated sequences can be used as reagents in an immunoassay. These polypeptides also are candidate subunit antigens in compositions for antiserum production or vaccines. While these truncated sequences can be produced by various known treatments of native viral protein, it is generally preferred to make synthetic or recombinant polypeptides comprising an HCV sequence. Polypeptides comprising these truncated HCV sequences can be made up entirely of HCV sequences (one or more epitopes, either contiguous or noncontiguous), or HCV sequences and heterologous sequences in a fusion protein. Useful heterologous sequences include sequences that provide for secretion from a recombinant host, enhance the immunological reactivity of the HCV epitope(s), or facilitate the coupling of the polypeptide to an immunoassay support or a vaccine carrier. See, e.g., EPO Pub. No. 116,201; U.S. Pat. No. 4,722,840; EPO Pub. No. 259,149; U.S. Pat. No. 4,629,783, the disclosures of which are incorporated herein by reference.

The size of polypeptides comprising the truncated HCV sequences can vary widely, the minimum size being a sequence of sufficient size to provide an HCV epitope, while the maximum size is not critical. In some applications, the maximum size usually is not substantially greater than that required to provide the desired HCV epitopes and function (s) of the heterologous sequence, if any. Typically, the truncated acid HCV amino acid sequence will range from about 5 to about 100 amino acids in length. More typically, however, the HCV sequence will be a maximum of about 50 amino acids in length, preferably a maximum of about 30 amino acids. It is usually desirable to select HCV sequences of at least about 10, 12 or 15 amino acids, up to a maximum of about 20 or 25 amino acids.

Truncated HCV amino acid sequences comprising epitopes can be identified in a number of ways. For example, the entire viral protein sequence can be screened by preparing a series of short peptides that together span the entire protein sequence. By starting with, for example, 100-mer polypeptides, it would be routine to test each polypeptide for the presence of epitope(s) showing a desired reactivity, and then testing progressively smaller and overlapping fragments from an identified 100-mer to map the epitope of interest. Screening such peptides in an immunoassay is within the skill of the art. It is also known to carry out a computer analysis of a protein sequence to identify potential epitopes, and then prepare oligopeptides comprising the identified regions for screening. It is appreciated by those of skill in the art that such computer analysis of antigenicity does not always identify an epitope that actually exists, and can also incorrectly identify a region of the protein as containing an epitope.

The observed relationship of the putative polyproteins of HCV and the Flaviviruses allows a prediction of the putative domains of the HCV "non-structural" (NS) proteins. The locations of the individual NS proteins in the putative Flavivirus precursor polyprotein are fairly well-known. Moreover, these also coincide with observed gross fluctuations in the hydrophobicity profile of the polyprotein. It is established that NS5 of Flaviviruses encodes the virion polymerase, and that NS1 corresponds with a complement fixation antigen which has been shown to be an effective vaccine in animals. Recently, it has been shown that a flaviviral protease function resides in NS3. Due to the observed similarities between HCV and the Flaviviruses, deductions concerning the approximate locations of the corresponding protein domains-and functions in the HCV polyprotein are possible. FIG. 11 is a schematic of putative domains of the HCV polyprotein. The expression of polypeptides containing these domains in a variety of recombinant host cells, including, for example, bacteria, yeast, insect, and vertebrate cells, should give rise to important immunological reagents which can be used for diagnosis, detection, and vaccines.

Although the non-structural protein region of the putative polyproteins of the HCV isolate described herein and of Flaviviruses appears to be generally similar, there is less similarity between the putative structural regions which are towards the N-terminus. In this region, there is a greater divergence in sequence, and in addition, the hydrophobic profile of the two regions show less similarity. This "divergence" begins in the N-terminal region of the putative NS1 domain in HCV, and extends to the presumed N-terminus. Nevertheless, it is still possible to predict the approximate locations of the putative nucleocapsid (N-terminal basic domain) and E (generally hydrophobic) domains within the. HCV polyprotein. From these predictions it may be possible to identify approximate regions of the HCV polyprotein that could correspond with useful immunological reagents. For example, the E and NS1 proteins of Flaviviruses are known to have efficacy as protective vaccines. These regions, as well as some which are shown to be antigenic in the HCV1, for example those within putative NS3, C, and NS5, etc., should also provide diagnostic reagents.

The immunogenicity of the HCV sequences may also be enhanced by preparing the sequences fused to or assembled with particle-forming proteins such as, for example, hepatitis B surface antigen or rotavirus VP6 antigen. Constructs wherein the HCV epitope is linked directly to the particle-forming protein coding sequences produce hybrids which are immunogenic with respect to the HCV epitope. In addition, all of the vectors prepared include epitopes specific to HBV, having various degrees of immunogenicity, such as, for example, the pre-S peptide. Thus, particles constructed from particle forming protein which include HCV sequences are immunogenic with respect to HCV and particle-form protein. See, e.g., U.S. Pat. No. 4,722,840; EPO Pub No. 175,261; EPO Pub. No. 259,149; Michelle et al. (1984) Int. Symposium on Viral Hepatitis.

Vaccines may be prepared from one or more immunogenic polypeptides derived from HCV/J1 or HCV/J7. The observed homology between HCV and Flaviviruses provides information concerning the polypeptides which are likely to be most effective as vaccines, as well as the regions of the genome in which they are encoded. The general structure of the Flavivirus genome is discussed in Rice et al. (1986) in THE VIRUSES: THE TOGAVIRIDAE AND FLAVIVIRIDAE (Series eds. Fraenkel-Conrat and Wagner, Vol eds. Schlesinger and Schlesinger, Plenum Press). The flavivirus genomic RNA is believed to be the only virus-specific mRNA species, and it is translated into the three viral structural proteins, i.e., C, M, and E, as well as two large nonstructural proteins, NV4 and NV5, and a complex set of smaller nonstructural proteins. It is known that major neutralizing epitopes for Flaviviruses reside in the E (envelope) protein. Roehrig (1986) in THE VIRUSES: THE TOGAVIRIDAE AND FLAVIVIRIDAE (Series eds. Fraenkel-Conrat and Wagner, Vol eds. Schlesinger and Schlesinger, Plenum Press). The corresponding HCV E gene and polypeptide encoding region may be predicted, based upon the homology to Flaviviruses. Thus, vaccines may be comprised of recombinant polypeptides containing epitopes of HCV E. These polypeptides may be expressed in bacteria, yeast, or mammalian cells, or alternatively may be isolated from viral preparations. It is also anticipated that the other structural proteins may also contain epitopes which give rise to protective anti-HCV antibodies. Thus, polypeptides containing the epitopes of E, C, and M may also be used, whether singly or in combination, in HCV vaccines.

In addition to the above, it has been shown that immunization with NS1 (nonstructural protein 1), results in protection against yellow fever. Schlesinger et al (1986) J. Virol. 60:1153. This is true even though the immunization does not give rise to neutralizing antibodies. Thus, particularly since this protein appears to be highly conserved among Flaviviruses, it is likely that HCV NS1 will also be protective against HCV infection. Moreover, it also shows that nonstructural proteins may provide protection against viral pathogenicity, even if they do not cause the production of neutralizing antibodies.

In view of the above, multivalent vaccines against HCV may be comprised of one or more epitopes from one or more structural proteins, and/or one or more epitopes from one or more nonstructural proteins. These vaccines may be comprised of, for example, recombinant HCV polypeptides and/or polypeptides isolated from the virions. In particular, vaccines are contemplated comprising one or more of the following HCV proteins, or subunit antigens derived therefrom: E,. NS1, C, NS2, NS3, NS4 and NS5. Particularly preferred are vaccines comprising E and/or NS1, or subunits thereof. In addition, it may be possible to use inactivated HCV in vaccines; inactivation may be by the preparation of viral lysates, or by other means known in the art to cause inactivation of Flaviviruses, for example, treatment with organic solvents or detergents, or treatment with formalin. Moreover, vaccines may also be prepared from attenuated HCV strains or from hybrid viruses such as vaccinia vectors known in the art [Brown et al. Nature 319: 549–550 (1986)].

The preparation of vaccines which contain immunogenic polypeptide(s) as active ingredients is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycerol-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing an HCV antigenic sequence resulting from administration of this polypeptide in vaccines which are also comprised of the various adjuvants.

The vaccines are conventionally administered parenterally, by injection, usually, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25%–70%.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine,. 2-ethylamino ethanol, histidine, procaine, and the like.

The vaccines are administered in a manner compatible with the dosage formulation, and in such amount as will be prophylactically and/or therapeutically effective. The quantity to be administered, which is generally in the range of 5 micrograms to 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be peculiar to each subject.

The vaccine may be given in a single dose schedule, or preferably in a multiple dose schedule. A multiple dose schedule is one in which a primary course of vaccination may be with 1–10 separate doses, followed by other doses given at subsequent time intervals required to maintain and or reenforce the immune response, for example, at 1–4 months for a second dose, and if needed, a subsequent dose(s) after several months. The dosage regimen will also, at least in part, be determined by the need of the individual and be dependent upon the judgment of the practitioner.

In addition, the vaccine containing the immunogenic HCV antigen(s) may be administered in conjunction with other immunoregulatory agents, for example, immune globulins.

The immunogenic polypeptides prepared as described above are used to produce antibodies, both polyclonal and monoclonal. If polyclonal antibodies are desired, a selected mammal (e.g., mouse, rabbit, goat, horse, etc.) is immunized with an immunogenic polypeptide bearing an HCV epitope (s). Serum from the immunized animal is collected and treated according to known procedures. If serum containing polyclonal antibodies to an HCV epitope contains antibodies to other antigens, the polyclonal antibodies can be purified by immunoaffinity chromatography. Techniques for producing and processing polyclonal antisera are known in the art, see for example, Mayer and Walker, eds. (1987) IMMUNOCHEMICAL METHODS IN CELL AND MOLECULAR BIOLOGY (Academic Press, London).

Monoclonal antibodies directed against HCV epitopes can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al. (1980) HYBRIDOMA TECHNIQUES; Hammerling et al. (1981), MONOCLONAL ANTIBODIES AND T-CELL HYBRIDOMAS; Kennett et al. (1980) MONOCLONAL ANTIBODIES; see also, U.S. Pat. Nos. 4,341,761; 4,399,121; 4,427,783; 4,444,887; 4,466,917; 4,472,500; 4,491,632; and 4,493,890. Panels of monoclonal antibodies produced against HCV epitopes can be screened for various properties; i.e., for isotype, epitope affinity, etc.

Antibodies, both monoclonal and polyclonal, which are directed against HCV epitopes are particularly useful in diagnosis, and those which are neutralizing are useful in passive immunotherapy. Monoclonal antibodies, in particular, may be used to raise anti-idiotype antibodies.

Anti-idiotype antibodies are immunoglobulins which carry an "internal image" of the antigen of the infectious agent against which protection is desired. Techniques for raising anti-idiotype antibodies are known in the art. See, e,g,, Grzych (1985), Nature 316:74; MacNamara et al. (1984), Science 226:1325, Uytdehaag et al (1985), J. Immunol. 134:1225. These anti-idiotype antibodies may also be useful for treatment and/or diagnosis of NANBH, as well as for an elucidation of the immunogenic regions of HCV antigens.

Using the HCV/J1 or HCV/J7 polynucleotide sequences as a basis, oligomers of approximately 8 nucleotides or more can be prepared, either by excision or synthetically, which hybridize with the HCV genome and are useful in identification of the viral agent(s), further characterization of the viral genome(s), as well as in detection of the virus(es) in diseased individuals. The probes for HCV polynucleotides (natural or derived) are a length which allows the detection of unique viral sequences by hybridization. While 6–8 nucleotides may be a workable length, sequences of about 10–12 nucleotides are preferred, and about 20 nucleotides appears optimal. These probes can be prepared using routine methods, including automated oligonucleotide synthetic methods. Among useful probes, for example, are the clones disclosed herein, as well as the various oligomers useful in probing cDNA libraries, set forth below. A complement to any unique portion of the HCV genome will be satisfactory. For use as probes, complete complementarity is desirable, though it may be unnecessary as the length of the fragment is increased.

For use of such probes as diagnostics, the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. The probes are then labeled. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies. Usually high stringency conditions are desirable in order to prevent false positives. The stringency of hybridization is determined by a number of factors during hybridization and during the washing procedure, including temperature, ionic strength, length of time, and concentration of formamide. These factors are outlined in, for example, Maniatis, T. (1982) MOLECULAR CLONING; A LABORATORY MANUAL (Cold Spring Harbor Press, Cold Spring Harbor, N.Y.).

Generally, it is expected that the HCV genome sequences will be present in serum of infected individuals at relatively low levels, i.e., at approximately $10^2$–$10^3$ chimp infectious doses (CID) per ml. This level may require that amplification techniques be used in hybridization assays. Such techniques are known in the art. For example, the Enzo Biochemical Corporation "Bio-Bridge" system uses terminal deoxynucleotide transferase to add unmodified 3'-poly-dT-tails to a DNA probe. The poly dT-tailed probe is hybridized to the target nucleotide sequence, and then to a biotin-modified poly-A. PCT App. No. 84/03520 and EPO Pub. No. 124,221 describe a DNA hybridization assay in which: (1) analyte is annealed to a single-stranded DNA probe that is complementary to an enzyme-labeled oligonucleotide; and (2) the resulting tailed duplex is hybridized to an enzyme-labeled oligonucleotide. EPO Pub. No. 204,510 describes a DNA hybridization assay in which analyte DNA is contacted with a probe that has a tail, such as a poly-dT tail, an amplifier strand that has a sequence that hybridizes to the tail of the probe, such as a poly-A sequence, and which is capable of binding a plurality of labeled strands.

A particularly desirable technique may first involve amplification of the target HCV sequences in sera approximately 10,000-fold, i.e., to approximately $10^6$ sequences/ml. This may be accomplished, for example, by the polymerase chain reactions (PCR) technique described by Saiki et al. (1986) Nature 324:163, Mullis, U.S. Pat. No. 4,683,195, and Mullis et al. U.S. Pat. No. 4,683,202. The amplified sequence(s) may then be detected using a hybridization assay which is described in co-pending European Publication No. 317-077 and Japanese application No. 63-260347, which are assigned to the herein assignee, and are hereby incorporated herein by reference. These hybridization assays, which should detect sequences at the level of $10^6$/ml, utilize nucleic acid multimers which bind to single-stranded analyte nucleic acid, and which also bind to a multiplicity of single-stranded labeled oligonucleotides. A suitable solution phase sandwich assay which may be used with labeled polynucleotide probes, and the methods for the preparation of probes is described in EPO Pub. No. 225,807 which is hereby incorporated herein by reference.

The probes can be packaged into diagnostic kits. Diagnostic kits include the probe DNA, which may be labeled; alternatively, the probe DNA may be unlabeled and the ingredients for labeling may be included in the kit in separate containers. The kit may also contain other suitably packaged reagents and materials needed for the particular hybridization protocol, for example, standards, wash buffers, as well as instructions for conducting the test.

Both the HCV/J1 or HCV/J7 polypeptides which react immunologically with serum containing HCV antibodies and the antibodies raised against the HCV specific epitopes in these polypeptides are useful in immunoassays to detect presence of HCV antibodies, or the presence of the virus and/or viral antigens, in biological samples. Design of the immunoassays is subject to a great deal of variation, and a variety of these are known in the art. An immunoassay for anti-HCV antibody may utilize one viral epitope or several viral epitopes. When multiple epitopes are used, the epitopes may be derived from the same or different viral polypeptides, and may be in separate recombinant or natural polypeptides, or together in the same recombinant polypeptides.

An immunoassay for viral antigen may use, for example, a monoclonal antibody directed towards a viral epitope, a combination of monoclonal antibodies directed towards epitopes of one viral polypeptide, monoclonal antibodies directed towards epitopes of different viral polypeptides, polyclonal antibodies directed towards the same viral antigen, polyclonal antibodies directed towards different viral antigens or a combination of monoclonal and polyclonal antibodies.

Immunoassay protocols may be based, for example, upon competition, or direct reaction, or sandwich type assays. Protocols may also, for example, use solid supports, or may be by immunoprecipitation. Most assays involve the use of labeled antibody or polypeptide. The labels may be, for example, fluorescent, chemiluminescent, radioactive, or dye molecules. Assays which amplify the signals from the probe are also known. Examples of which are assays which utilize biotin and avidin, and enzyme-labeled and mediated immunoassays, such as ELISA assays.

Typically, an immunoassay for anti-HCV antibody will involve selecting and preparing the test sample, such as a biological sample, and then incubating it with an antigenic (i.e., epitope-containing) HCV polypeptide under conditions that allow antigen-antibody complexes to form. Such conditions are well known in the art. In a heterogeneous format, the polypeptide is bound to a solid support to facilitate separation of the sample from the polypeptide after incubation. Examples of solid supports that can be used are nitrocellulose, in membrane or microtiter well form, polyvinylchloride, in sheets or microtiter wells, polystyrene latex, in beads or microtiter plates, polyvinylidine fluoride, known as Immobulon™, diazotized paper, nylon membranes, activated beads, and Protein A beads. Most preferably, heterogeneous assays are performed using either Immulon™ 1 microtiter plates (Dynatech) or specular-finished 0.25-inch polystyrene beads (available from Precision Plastic Ball). The solid support is typically washed after separating it from the test sample. In a homogeneous format, the test sample is incubated with antigen in solution, under conditions that will precipitate any antigen-antibody complexes that are formed, as is known in the art. The precipitated complexes are then separated from the test sample, for example, by centrifugation. The complexes formed comprising anti-HCV antibody are then detected by any of a number of techniques. Depending on the format, the complexes can be detected with labeled anti-xenogeneic Ig or, if a competitive format is used, by measuring the amount of bound, labeled competing antibody.

In immunoassays where HCV polypeptides are the analyte, the test sample, typically a biological sample, is incubated with anti-HCV antibodies again under conditions that allow the formation of antigen-antibody complexes. Various formats can be employed, such as the "sandwich" assay. In this assay, antibody is bound to a solid support, incubated with a test sample, washed, incubated with a labeled anti-analyte antibody, and washed again. Analyte is detected by determining if the second antibody is bound to the support. In a competitive format, which can be either heterogeneous or homogeneous, a test sample is usually incubated with and antibody and a labeled, competing antigen either sequentially or simultaneously. These and other formats are well known in the art.

The Flavivirus model for HCV allows predictions regarding the likely location of diagnostic epitopes for the virion structural proteins. The C, pre-M, M, and E domains are all likely to contain epitopes of significant potential for detecting viral antigens, and particularly for diagnosis. Similarly, domains of the nonstructural proteins are expected to contain important diagnostic epitopes (e.g., NS5 encoding a putative polymerase; and NS1 encoding a putative complement-binding antigen). Recombinant polypeptides, or viral polypeptides, which include epitopes from these specific domains may be useful for the detection of viral antibodies in infectious blood donors and infected patients. In addition, antibodies directed against the E and/or M proteins can be used in immunoassays for the detection of viral antigens in patients with HCV caused NANBH, and in infectious blood donors. Moreover, these antibodies may be extremely useful in detecting acute-phase donors and patients.

Antigenic regions of the putative polyprotein can be mapped and identified by screening the antigenicity of bacterial expression products of HCV cDNAs which encode portions of the polyprotein. Other antigenic regions of HCV may be detected by expressing the portions of the HCV cDNAs in other expression systems, including yeast systems and cellular systems derived from insects and vertebrates. In addition, studies giving rise to an antigenicity index and hydrophobicity/hydrophilicity profile give rise to information concerning the probability of a region's antigenicity. Efficient detection systems may include the use of panels of epitopes. The epitopes in the panel may be constructed into one or multiple polypeptides.

Kits suitable for immunodiagnosis and containing the appropriate labeled reagents are constructed by packaging the appropriate materials, including the polypeptides of the invention containing HCV epitopes or antibodies directed against HCV epitopes in suitable containers, along with the remaining reagents and materials required for the conduct of the assay (e.g., wash buffers, detection means like labeled anti-human Ig, labeled anti-HCV, or labeled HCV antigen), as well as a suitable set of assay instructions.

The HCV/J1 and HCV/J7 nucleotide sequence information described herein may be used to gain further information on the sequence of the HCV genomes, and for identification and isolation of additional HCV isolates related to J1 or J7. This information, in turn, can lead to additional polynucleotide probes, polypeptides derived from the HCV genome, and antibodies directed against HCV epitopes which would be useful for the diagnosis and/or treatment of HCV caused NANBH.

The HCV/J1 and HCV/J7 nucleotide sequence information herein is useful for the design of probes for the isolation of additional sequences which are derived from as yet undefined regions of the HCV genomes from which the J1 and J7 sequences are derived. For example, labeled probes containing a sequence of approximately 8 or more nucleotides, and preferably 20 or more nucleotides, which are derived from regions close to the 5'-termini or 3'-termini of the family of HCV cDNA sequences disclosed in the examples may be used to isolate overlapping cDNA sequences from HCV cDNA libraries. These sequences which overlap the cDNAs in the above-mentioned clones, but which also contain sequences derived from regions of the genome from which the cDNA in the above mentioned clones are not derived, may then be used to synthesize probes for identification of other overlapping fragments which do not necessarily overlap the cDNAs described below. Methods for constructing cDNA libraries are known in the art. See, e.g. EPO Pub. No. 318,216 and 388,232. It is particularly preferred to prepare libraries from the serum of Japanese and other Asian patients diagnosed as having NANBH demonstrating antibody to HCV1 antigens; these are believed to be the most likely candidates for carriers of HCV/J1, HCV/J7, or related isolates.

HCV particles may be isolated from the sera from individuals with NANBH or from cell cultures by any of the methods known in the art, including for example, techniques based on size discrimination such as sedimentation or exclusion methods, or techniques based on density such as ultracentrifugation in density gradients, or precipitation with agents such as polyethylene glycol, or chromatography on a variety of materials such as anionic or cationic exchange materials, and materials which bind due to hydrophobicity.

A preferred method of isolating HCV particles or antigen is by immunoaffinity columns. Techniques for immunoaffinity chromatography are known in the art, including techniques for affixing antibodies to solid supports so that they retain their immunoselective activity. The techniques may be those in which the anti-bodies are adsorbed to the support (see, for example, Kurstak in ENZYME IMMUNODIAGNOSIS, page 31–37), as well as those in which the antibodies are covalently linked to the support. Generally, the techniques are similar to those used for covalent linking of antigens to a solid support, described above. However, spacer groups may be included in the bifunctional coupling agents so that the antigen binding site of the antibody remains accessible. The antibodies may be monoclonal, or polyclonal, and it may be desirable to purify the antibodies before their use in the immunoassay.

The general techniques used in extracting the genome from a virus, preparing and probing a cDNA library, sequencing clones, constructing expression vectors, transforming cells, performing immunological assays such as radioimmunoassays and. ELISA assays, for growing cells in culture, and the like are known in the art and laboratory manuals are available describing these techniques. However, as a general guide, the following sets forth some sources currently available for such procedures, and for materials useful in carrying them out.

Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the Beta-lactamase (penicillinase) and lactose promoter systems (Chang et al. (1977), Nature 198:1056), the tryptophan (trp) promoter system (Goeddel et al. (1980) Nucleic Acid Res. 8:4057), the lambda-derived $P_L$ promoter and N gene ribosome binding site (Shimatake et al. (1981) Nature 292:128) and the hybrid tac promoter (De Boer et al. (1983) Proc. Natl. Acad. Sci. U.S.A. 292:128) derived from sequences of the trp and lac UV5 promoters. The foregoing systems are particularly compatible with *E. coli*; if desired, other prokaryotic hosts such as strains of Bacillus or Pseudomonas may be used, with corresponding control sequences.

Eukaryotic hosts include yeast and mammalian cells in culture systems. *Saccharomyces cerevisiae, Saccharomyces carlsbergensis, Klebsiela lactis* and *Pichia pastoris* are the most commonly used yeast hosts, and are convenient fungal hosts. Yeast compatible vectors carry markers which permit selection of successful transformants by conferring prototrophy to auxotrophic mutants or resistance to heavy metals on wild-type strains. Yeast compatible vectors may employ the 2 micron origin of replication (Broach et al. (1983) Math Enz. 101:307), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess et al. (1968) J. Adv. Enzyme Eng. 7:149; Holland et al. (1978), J. Biol. Chem. 256:1385), including the promoter for 3 phosphoglycerate kinase (Hitzeman (1980), J. Biol. Chem. 255:2073). Terminators may also be included, such as those derived from the enolase gene (Holland (1981), J. Biol. Chem. 256:1385). Particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, leader sequence from yeast alpha factor. In addition, the transcriptional regulatory region and the transcriptional initiation region which are operably linked may be such that they are not naturally associated in the wild-type organism. These systems are described in detail in EPO Pub. No. 120,551; EPO Pub. No. 116,201; and EPO Pub. No. 164,556 all of which are incorporated herein by reference.

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40) (Fiers (1978), Nature 273:113), Rous sarcoma virus (RSV), adenovirus (ADV), and bovine papilloma virus (BPV). Mammalian cells may also require terminator sequences and poly A addition sequences; enhancer sequences which increase expression may also be included, and sequences which cause amplification of the gene may also be desirable. These sequences are known in the art. Vectors suitable for replication in mammalian cells may include viral replicons, or sequences which insure integration of the appropriate sequences encoding NANBV epitopes into the host genome.

The vaccinia virus system can also be used to express foreign DNA in mammalian cells. To express heterologous genes, the foreign DNA is usually inserted into the thymidine kinase gene of the vaccinia virus and then infected cells can be selected. This procedure is known in the art and further information can be found in these references [Mackett et al. J. Virol. 49: 857–864 (1984) and Chapter 7 in *DNA Cloning*, Vol. 2, IRL Press].

In addition, viral antigens can be expressed in insect cells by the Baculovirus system. A general guide to Baculovirus expression by Summer and Smith is *A Manual of Methods for Baculovirus Vectors and Insect Cell Culture Procedures* (Texas Agricultural Experiment Station Bulletin No. 1555). To incorporate the heterologous gene into the Baculovirus genome the gene is first cloned into a transfer vector containing some Baculovirus sequences. This transfer vector, when it is cotransfected with wild-type virus into insect cells, will recombine with the wild-type virus. Usually, the transfer vector will be engineered so that the heterologous gene will disrupt the wild-type Baculovirus polyhedron gene. This disruption enables easy selection of the recombinant virus since the cells infected with the recombinant virus will appear phenotypically different from the cells infected with the wild-type virus. The purified recombinant virus can be used to infect cells to express the heterologous gene. The foreign protein can be secreted into the medium if a signal peptide is linked in frame to the heterologous gene; otherwise, the protein will be bound in the cell lysates. For further information, see Smith et al Mol. & Cell. Biol. 3:2156–2165 (1983) or Luckow and Summers in Virology 17: 31–39 (1989).

Transformation may be by any method for introducing polynucleotides into a host cell, including, for example packaging the polynucleotide in a virus and transducing a host cell with the virus, and by direct uptake of the polynucleotide. The transformation procedure used depends upon the host to be transformed. Bacterial transformation by direct uptake generally employs treatment with calcium or rubidium chloride (Cohen (1972), Proc. Natl. Acad. Sci. U.S.A. 69:2110; Maniatis et al. (1982), MOLECULAR CLONING; A LABORATORY MANUAL (Cold Spring Harbor Press, Cold Spring Harbor, N.Y.). Yeast transformation by direct uptake may be carried out using the method of Hinnen et al. (1978) Proc. Natl. Acad. Sci. U.S.A. 75: 1929. Mammalian transformations by direct uptake may be conducted using the calcium phosphate precipitation method of Graham and Van der Eb (1978), Virology 52:546 or the various known modifications thereof.

Vector construction employs techniques which are known in the art. Site-specific DNA cleavage is performed by treating with suitable restriction enzymes under conditions which generally are specified by the manufacturer of these commercially available enzymes. The cleaved fragments may be separated using polyacrylamide or agarose gel electrophoresis techniques, according to the general procedures found in Methods in Enzymology (1980) 65:499–560. Sticky ended cleavage fragments may be blunt ended using *E. coli* DNA polymerase I (Klenow) in the presence of the appropriate deoxynucleotide triphosphates (dNTPs) present in the mixture. Treatment with S1 nuclease may also be used, resulting in the hydrolysis of any single stranded DNA portions.

Ligations are carried out using standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate and thus prevent religation of the vector; alternatively, restriction enzyme digestion of unwanted fragments can be used to prevent ligation. Ligation mixtures are transformed into suitable cloning hosts, such as *E. coli*, and successful transformants selected by, for example, antibiotic resistance, and screened for the correct construction.

Synthetic oligonucleotides may be prepared using an automated oligonucleotide synthesizer as described by Warner (1984), DNA 3:401. If desired, the synthetic strands may be labeled with $^{32}P$ by treatment with polynucleotide kinase in the presence of $^{32}P$-ATP, using standard conditions for the reaction. DNA sequences, including those isolated from cDNA libraries, may be modified by known techniques, including, for example site directed mutagenesis, as described by Zoller (1982), Nucleic Acids Res. 10:6487.

DNA libraries may be probed using the procedure of Grunstein and Hogness (1975), Proc. Natl. Acad. Sci. U.S.A. 73:3961. Briefly, in this procedure, the DNA to be probed is immobilized on nitrocellulose filters, denatured, and prehybridized with a buffer. The percentage of formamide in the buffer, as well as the time and temperature conditions of the prehybridization and subsequent hybridization steps depends on the stringency required. Oligomeric probes which require lower stringency conditions are generally used with low percentages of formamide, lower temperatures, and longer hybridization times. Probes containing more than 30 or 40 nucleotides such as those derived from cDNA or genomic sequences generally employ higher temperatures, e.g., about 40°–42° C., and a high percentage, e.g., 50%, formamide. Following prehybridization, 5'-$^{32}P$-labeled oligonucleotide probe is added to the buffer, and the filters are incubated in this mixture under hybridization conditions. After washing, the treated filters are subjected to autoradiography to show the location of the hybridized probe; DNA in corresponding locations on the original agar plates is used as the source of the desired DNA.

An enzyme-linked immunosorbent assay (ELISA) can be used to measure either antigen or antibody concentrations. This method depends upon conjugation of an enzyme to either an antigen or an antibody, and uses the bound enzyme activity as a quantitative label. To measure antibody, the known antigen is fixed to a solid phase (e.g., a microplate or plastic cup), incubated with test serum dilutions, washed, incubated with anti-immunoglobulin labeled with an enzyme, and washed again. Enzymes suitable for labeling are known in the art, and include, for example, horseradish peroxidase. Enzyme activity bound to the solid phase is measured by adding the specific substrate, and determining product formation or substrate utilization colorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is estimated colorimetrically, and related to antigen concentration.

EXAMPLES

I

This example describes the cloning of the HCV/J1 and HCV/J7 nucleotide sequences.

Both blood samples which were used as a source of HCV virions were found to be positive in an anti-HCV antibody assay. The HCV isolates from these samples were named HCV/J1 and HCV/J7. The infectivity of the blood sample containing the J1 isolate was confirmed by a prospective study of blood transfusion recipients. Dr. Tohru Katayama from the Department of Surgery at the National Tokyo Chest Hospital collected blood from patients who have contracted post-transfusion non-A, non-B hepatitis. He also collected blood samples from the respective blood donors of these patients. Next, these samples were assayed for antibodies to the C100-3 HCV1 antigen (EPO Pub. Nos. 318,216 and 388,232), and blood from one of the donors was found to be positive.

Isolation of the RNA from the blood samples began by pelleting virions in the blood sample by ultracentrifugation [Bradley, D. W., McCaustland, K. A., Cook E. H., Schable, C. A., Ebert, J. W. and Maynard, J. E. (1985) Gastroenterology 88, 773–779]. RNA was then extracted from the pellet by the:.guanidinium/cesium chloride method [Maniatis T., Fritsch, E. F., and Sambrook J. (1982) "Molecular Cloning: A Laboratory Manual", Cold Spring Harbor Laboratory, Cold Spring Harbor] and further purified by phenol/chloroform extraction in the presence of urea, [Berk, A. J. Lee, F., Harrison, T., Williams, J. and Sharp, P. A. (1979) Cell 17, 935–944].

Five pairs of synthetic oligonucleotide primers were designed from the C/E, E, E/NS1, NS3, and NS5 domains of the nucleotide sequence of HCV1 to isolate fragments from the J1 and J7 genome. The first set of primers were to isolate the sequence from the core and some of the envelope domain. The second set of primers were to isolate the sequences in the envelope domain. The third set of primers were to isolate a fragment which overlapped the putative envelope and non-structural one, NS1, domains. The fourth and fifth set of primers were used to isolate fragments from non-structural domains three and five, NS3 and NS5. The sequences for the various primers are shown below:

| The sequence of the primers for the C/E region were: | |
|---|---|
| 21S | 5' CGTGCCCCCGCAAGACTGCT 3' |
| J80A | 5' CCGTCCTCCAGAACCCGGAC 3' |
| The sequence of the primers for the E region were: | |
| 71S | 5' GCCGACCTCATGGGGTACAT 3' |
| J132A | 5' AACTGCGACACCACTAAGGC 3' |
| The sequence of the primers for the E/NS1 region were: | |
| 127S | 5' TGGCATGGGATATGATGATG 3' |
| 166A | 5' TTGAACTTGTGGTGATAGAA 3' |

-continued

| The sequence of the primers for the NS3 region were | |
|---|---|
| 464S | 5' GGCTATACCGGCGACTTCGA 3' |
| 526A | 5' GACATGCATGTCATGATGTA 3' |
| The sequence of the primers for the NS5 region were: | |
| 870S | 5' GCTGGAAAGAGGGTCTACTA 3' |
| 917A | 5' GTTCTTACTGCCCAGTTGAA 3' |

1 μg of the antisense primers, 166A, 526A, or 917A, was added to 10 units of reverse transcriptase (Biorad) to synthesize cDNA fragments from the isolated RNA as the template. The cDNA fragments were then amplified by a standard polymerase chain reaction [Saiki, R. K., Scharf, S., Faloona, F., Mullis, K. B., Horn G. T., Erlich, H. A., and Arnheim, N. (1985) Science 230, 1350–1354] after 1 μg of the appropriate sense primer, 21S, 71S, 127S, 464S or 870S, was added.

The cDNA fragments amplified by the PCR method were gel isolated and cloned by blunt-end ligation into the SmaI site of pUC119 [Vieira, J. and Messing, J. (1987) Methods in Enzymology 153, 3–11] or into the SnaBI site of charomid SB, a derivative of the cloning vector charomid 9–42 [Saito, I. and Stark, G. (1986) Proc. Natl. Acad. Sci. U.S.A. 83: 8664–8668]. Clones which contain the fragments of the five viral domains were successfully constructed.

II

From the PCR reaction of the Japanese isolates, J1 and J7, three independent clones from each region, C/E, E, E/NS1, NS3, and NS5, have been sequenced by the dideoxy chain termination method.

Sequence from all regions except C/E has been isolated from the J1 isolate. Sequence from only the C/E region has been isolated from the J7 isolate. Surprisingly, fragments isolated from both isolates are neither longer or shorter than what would be predicted from the HCV1 genome. However, there is heterogeneity between clones containing sequence from the same region. Consequently, a consensus sequence was constructed for each of the domains, C/E, E, E/NS1, NS3 and NS5, as shown respectively in FIGS. 1 through 5. These differences may be explained as artifacts which occur randomly during the PCR amplification [Saiki, R. K., Scharf, S., Faloona, F., Mullis, K. B., Horn, G. T., Erlich, H. A., and Arnheim, N. (1985) Science 230, 1350–1354]. Another explanation is that more than one virus genome is present in the plasma of a single healthy carrier and that these genomes are heterogeneous at the nucleotide level.

To clarify this point, it was determined how many of these nucleotide differences would lead to amino acid changes, using the sequence from the NS3 domain of the J1 isolate as an example. Out of the five nucleotide differences, three fall on the third position of the amino acid codon and do not change the amino acid sequence. Both of the remaining two nucleotide changes fall on the first position of the amino acid codon and generate amino acid changes of threonine to alanine and proline to alanine, all of which are small, neutral amino acid residues. Similarly, when analyzing the nucleotide differences in other domains, many silent and conserved mutations are found. These results suggest that nucleotide sequences of the HCV genomes in the plasma of a single healthy donor are heterogeneous at the nucleotide level.

Figure 7:
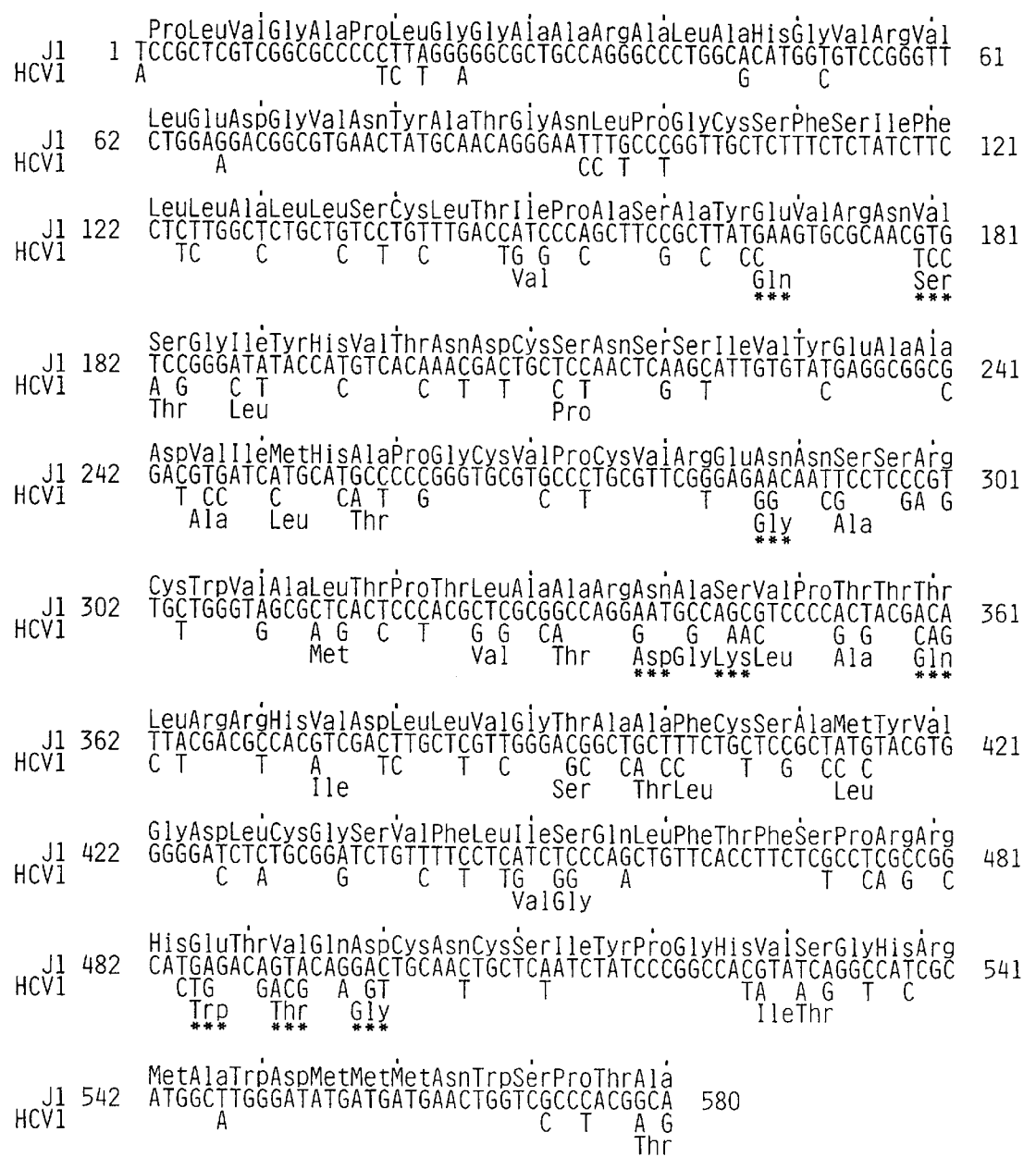

In addition, once the consensus sequences for each of the fragments were compiled each sequence was compared to the HCV1 isolate in FIGS. 6 through 10. In FIG. 6 the fragment from the C/E region of the J7 isolate shows a 92.8%, 512/552, nucleotide and 97.4%, 150/154, amino acid homology to the HCV1 isolate. The fragment from the E domain of J1 shows a slightly lower nucleotide and amino acid homology to HCV1 in FIG. 7 of 76.2% and 82.9%, respectively. The fragment from the J1 isolate which overlaps the envelope and non-structural one domains shows the lowest homology to HCV1, as seen in FIG. 8, where the J1 isolate has a 71.5% nucleotide homology and a 73.5% amino acid homology to HCV1. FIG. 9 shows a comparison of the fragment from the NS3 domain of J1 to HCV1. The homology between the nucleotides sequences is 79.8%, while the amino acid homology between the isolates is quite high, 92.2% or 179/194 amino acids. FIG. 10 shows the homology between the NS5 sequences from J1 and HCV1. The sequences have a 84.3% nucleotide and 88.7% amino acid homology.

The vectors described in the examples above were deposited with the Patent Microorganism Depository, Fermentation Institute, Agency of Industrial Science and Technology at 1–3, Higashi 1-chome Tsukuba-chi, Ibaragiken 305, Japan, and will be maintained under the provisions of the Budapest Treaty. The accession numbers and dates of the deposit are listed below, on page 68.

III

Clone J1-1519, containing J1 sequences homologous to nucleotides 1612 to 1978 HCV-1, was isolated using the essentially the techniques described above. However, primers J159S and 199A were used for the cloning of J1-1519. Primer J159S, consisting of 20 nucleotides, is a sense primer whose sequence, 5' to 3', is identical to nucleotides 301 to 320 of the J1 sequence shown in FIG. 3. Primer 199A, consisting of 20 nucleotides, is an anti-sense primer whose sequence, 5' to 3', is identical to the reverse complement of nucleotides 1979 to 1998 of HCV-1.

The sequences of the oligomeric primers J159S and 199A, which follow, were based upon those in J1-1216 and in HCV1.

| J159S | 5' ACT GCC CTG AAC TGC AAT GA 3' |
|---|---|
| 199A | 5' AAT CCA GTT GAG TTC ATC CA 3' |

Three independent clones spanning this region were sequenced; the sequences in this region obtained from the three clones were identical. The DNA sequence of the HCV cDNA in J1-1519 the amino acids encoded therein (shown above the nucleotide sequence) are shown in FIG. 13. The homology between the J1-1519 and HCV1 cDNA is approximately 70% at the nucleotide level, and about 75% at the amino acid level.

Cloned material containing the J1/1519 HCV cDNA (pS1-1519) has been maintained in DH5α, and deposited with the Patent Microorganism Depository.

IV

DNA sequences from the E/NS1 and the NS3/NS4 domains of the J1 isolate were isolated and sequenced using asymmetric PCR methods and the M13 dideoxy sequencing method. The plasma or sera was extracted with 50 μg/ml of poly A carrier or ms2 RNA by an acid guanidinium thiocyanate extraction described in Chomcyzski and Sacchi (1987), Analytical Biochemistry 162:156, or the RNA was also purified from plasma or sera by the Proteinase K/sodium dodecylsufate treatment. The procedure is as follows. Either 0.1 mL or 0.2 mL of plasma was diluted to a final volume of 1.0 mL, with a TENB/proteinase K/SDS solution (0.05M Tris-HCL, pH 8.0, 0.001M EDTA, 0.1M NaCl, 1 mg/mL Proteinase K, and 0.5% SDS) containing 10 μg/mL ms2 RNA, and incubated at 37° C. for 60 minutes. After this proteinase K digestion, the resultant plasma fractions were deproteinized by extracting twice with saturated phenol/chloroform/isoamyl alcohol [1:1(50:1)], and then twice with an equal volume of a 50:1 mixture of chloroform/isoamyl alcohol. Following phase separation by centrifugation, the aqueous phase was brought to a final concentration of 0.2M Na Acetate, and the nucleic acids were precipitated by the addition of two volumes of 100% ethanol. The precipitated nucleic acids were recovered by centrifugation at 10K for 10 minutes at 4° C. in an Eppendorf microfuge. The RNA was heated to 65° C. for 2 to 5 minutes to disrupt secondary structure and then immediately cooled on ice. In a 25 μl reaction volume the RNA was transcribed into cDNA by incubating 1 μg of the appropriate primer(s), 40 units of RNase inhibitor (RNASIN® available from Fisher/Promega), 5 units of AMV reverse transcriptase, and any necessary salts or buffers. The final PCR products were usually the result of two or more rounds of PCR. The parameters of all PCR rounds consisted of 30 to 35 thermal cycles of 94° C. for 1minute, for denaturation, 45° C. for 2 minutes, for anealing, 72° C. for 3 minutes, for DNA extension. The last cycle includes a seven minute extension step at 72° C.

IV.A.

As described above, two rounds of PCR were performed on J1 RNA to clone the J1 DNA sequences homologous to nucleotides 5402 to 5526 of HCV1. The first round of PCR, PCRI, used primers 511/16A and 511/16B, described below, to clone J1 DNA sequences homologous to 5363 to 5563 of HCV1. The thermal cycle of PCRI were different than what was described above. The annealing temperature was changed to 37° C. all other parameters were the same. A tenth of the PCRI reaction volume was used the template for the second round of PCR, PCRII, where primers 511/35A and 511/35B, described below, were used. Again, the annealing temperature was changed from what is described above. The annealing temperature was 60° C. and all other parameters were the same.

The primers used in this experiment all contain sequences identical to HCV-1. However, for cloning ease or to anticipate J1 variability non HCV-1 sequences are sometimes included in particular primers. Primer 511/16A, consisting of 16 nucleotides, is a sense primer whose sequence, 5' to 3', is identical to nucleotides 5347 to 5362 of HCV-1. Primer 511/16B, consisting of 16 nucleotides, is an anti-sense primer whose sequence, 5' to 3', is the reverse complement of nucleotides 5564 to 5579. Primer 511/35A, consisting of 35 nucleotides, is a sense primer whose sequence, 5' to 3', begins with CTTGAATTC, and then the next 23 nucleotides are identical to nucleotides 5376 to 5401 of HCV-1. Primer 511/35B, consisting of 35 nucleotides, is an anti-sense primer whose sequence, 5' to 3', begins with CTTGAATTC, and then the next 23 nucleotides are identical to the reverse complement of nucleotides 5527 to 5552 of HCV-1.

The sequences of the primer described above are shown below:

| | |
|---|---|
| 511/16A | 5' AAC AGG CTG CGT GGT C 3' |
| 511/16B | 5' AGT TGG TCT GGA CAG C 3' |
| 511/35A | |
| 5' <u>CTTGAATTC</u> TCG TCT TGT CCG GGA AGC CGG CAA TC 3' | |
| 511/35B | |
| 5' <u>CTTGAATTC</u> CCT CTG CCT GAC GGG ACG CGG TCT GC 3' | |

The PCRII products were cut with EcoRI and then gel purified. The EcoRI fragment was cloned into M13 for sequencing purposes. The consensus sequence of all the clones sequences is shown in FIG. 16.

IV.B.

As described above, multiple rounds of PCR were performed on J1 RNA to clone the J1 DNA sequences homologous to nucleotides 1979 to 2239 of HCV1. Two separate rounds of PCR were performed first, PCRIa and PCRIb. PCRIa used primers J1(E2)3 and J1rc12, described below, to clone J1 DNA sequences homologous to nucleotides 1292 to 2296 of HCV1. PCRIb used primers J1(E)4 and J1rc12, described below, to clone J1 DNA sequences homologous to nucleotides 1426 to 2296. A tenth of the PCRIa and PCRIb reaction volumes was used the template for a second round of PCR, PCRII, where primers J1IZ-1 and J1rc13, described below, were used.

The primers used in this experiment contain sequences identical to either HCV1 or J1. However, for cloning ease non HCV-1 sequences are sometimes included in particular primers. Primer J1(E2)3, consisting of 30 nucleotides, is a sense primer whose sequence, 5' to 3', begins with CTTAGAATTG and continues with sequence identical to nucleotides 1272 to 1291 of HCV-1. Primer J1rc12, consisting of 27 nucleotides, is an anti-sense primer whose sequence, 5' to 3', begins with CTTGAATTC and continues with sequence identical to the reverse complement of nucleotides 2297 to 2314. Primer J1(E)4, consisting of 30 nucleotides, is a sense primer whose sequence, 5' to 3', begins with CTTAGAATTG and continues with sequence identical to nucleotides 1406 to 1425 of HCV-1. Primer J1IZ-1, consisting of 28 nucleotides, is a sense primer whose sequence, 5' to 3', begins with CTTGAATTC, and continues with sequence identical to nucleotides 349 to 367 of FIG. 13. Primer J1rc13, consisting of 31 nucleotides, is an anti-sense primer whose sequence, 5' to 3', begins with CTTAGAATTC, and continues with sequence identical to the reverse complement of nucleotides 2240 to 2260 of HCV-1.

The sequences of the above-mentioned primers are shown below:

The PCRII products were gel were pooled with the PCRII products of Example IV.C. and then were gel purified on a 7% PAGE cut with EcoRI. The fragments were further klenowed and cut with RsaI. This fragment was subcloned into a derivative of the commercially available vector, pGEM-3Z, in host HB101, and deposited with the ATCC as AW-300bp. The derivative vectors maintain an intact $Amp^r$ gene, and the genes required for replication in *E. coli*. The HCV cDNA fragment may be removed with SacI and XbaI. From the inserts from these bacterial clones were subcloned into M13 and sequenced. The consensus sequence of the inserts is shown in FIG. 15.

IV.C.

As described above, multiple rounds of PCR were performed on J1 RNA to clone the J1 DNA sequences homologous to nucleotides 1936 to 2239 of HCV1. Two separate rounds of PCR were performed first, PCRIa and PCRIb. PCRIa used primers J1(E2)3 and J1rc12, described below, to clone J1 DNA sequences homologous to nucleotides 1292 to 2296 of HCV1. PCRIb used primers J1(E)4 and J1rc12, described below, to clone J1 DNA sequences homologous to nucleotides 1426 to 2296. A tenth of the PCRIa and PCRIb reaction volumes was used the template for a second-round of PCR, PCRII, where primers J1IZ-2 and J1rc13, described below, were used.

The primers used in this experiment contain sequences identical to either HCV1 or J1. However, for cloning ease non HCV-1 sequences are sometimes included in particular primers. Primer J1(E2)3, consisting of 30 nucleotides, is a sense primer whose sequence, 5' to 3', begins with CTTAGAATTG and continues with sequence identical to nucleotides 1272 to 1291 of HCV-1. Primer J1rc12, consisting of 27 nucleotides, is an anti-sense primer whose sequence, 5' to 3', begins with CTTGAATTC and continues with sequence identical to the reverse complement of nucleotides 2297 to 2314. Primer J1(E)4, consisting of 30 nucleotides, is a sense primer whose sequence, 5' to 3', begins with CTTAGAATTG and continues with sequence identical to nucleotides 1406 to 1425 of HCV-1. Primer J1IZ-2, consisting of 21 nucleotides, is a sense primer whose sequence, 5' to 3', is identical to nucleotides 304 to 324 of FIG. 13. Primer J1rc13, consisting of 31 nucleotides, is an anti-sense primer whose sequence, 5' to 3', begins with CTTAGAATTC, and continues with sequence identical to the reverse complement of nucleotides 2240 to 2260 of HCV-1.

The sequences of the above-mentioned primers are shown below:

| | |
|---|---|
| J1(E2)3 | 5' CTTAGAATTC TGG CAT GGG ATA TGA TGA TG 3' |
| J1(E)4 | 5' CTTAGAATTC TCC ATG GTG GGG AAC TGG GC 3' |
| J1rc12 | 5' CTTGAATTC TAA CGG GCT GAG CTC GGA 3' |
| J1rc13 | 5' CTTAGAATTC CGT CCA GTT GCA GGC AGC TTC 3' |
| J1IZ-1 | 5' CTTGAATTC CAA CTG GTT CGG CTG TAC A 3' |

| J1(E2)3 | 5' CTTAGAATTC TGG CAT GGG ATA TGA TGA TG 3' |
|---|---|
| J1(E)4 | 5' CTTAGAATTC TCC ATG GTG GGG AAC TGG GC 3' |
| J1rc12 | 5' CTTGAATTC TAA CGG GCT GAG CTC GGA 3' |
| J1rc13 | 5' CTTAGAATTC CGT CCA GTT GCA GGC AGC TTC 3' |
| J1IZ-2 | 5' TGA GAC GGA CGT GCT GCT CCT 3' |

The PCRII products were gel were pooled with the PCRII products of Example IV.B. and then were gel purified on a 7% PAGE cut with EcoRI. The fragments were further klenowed and cut with RsaI. This fragment was subcloned into a derivative of the commercially available vector, pGEM-3Z, in host HB101, and deposited with the ATCC as AW-300 bp. The derivative vectors maintain an intact Amp$^r$ gene, and the genes required for replication in *E. coli*. The HCV cDNA fragment may be removed with SacI and XbaI. From the inserts from these bacterial clones were subcloned into M13 and sequenced. The consensus sequence of the inserts is shown in FIG. 15.

primer whose sequence, 5' to 3', begins with CTTGAATTC, and continues with sequence identical to the reverse complement of nucleotides 4639 to 4665 of HCV-1.

The sequences of the above-mentioned primers are shown below:

| J1C200-1 | 5' TCC TAC TTG AAA GGC TC 3' |
|---|---|
| J1C200-3 | 5' GGA TCC AAG CTG AAA TCG AC 3' |
| J1C200-2 | 5' CTTGAATTC CCC GTG GAG TGG CTA AGG CGG TGG ACT 3' |
| J1C200-4 | 5' CTTGAATTC TCG AAG TCG CCG GTA TAG CCG GTC ATG 3' |

Sequencing of the J1 DNA sequences was accomplished using an assymetric PCR technique, essentially as described in Shyamala and Ames, J. Bacteriology 171:1602 (1989). In this technique, amplification of the cDNA is carried out with a limiting concentration of one of the primers (usually in a ratio of about 1:50) in order to get preferential amplification of one strand. The preferentially amplified strand is then sequenced by the dideoxy chain termination method. The sequence of the PCR products is shown in FIG. 16.

The primers used for assymetric sequencing by the PCR method were either J1C200-2 and J1C200-7 or J1C200-4 and J1C200-6. The sequences of J1C200-6 and J1C200-7 are shown below.

IV.D.

As described above, two rounds of PCR were performed on J1 RNA to clone the J1 DNA sequences homologous to nucleotides 3904 to 4638 of HCV1. The first round of PCR, PCRI, was performed using primers J1C200-1 and J1C200-3, described below, to clone J1 DNA sequences homologous to nucleotides 3811 to 4703 of HCV1. Half of PCRI products were used as the template for a second round of PCR, PCRII, where primers J1C200-2 and J1C200-4, described below, were used.

| J1C200-6 | 5' CTTGAATTC CGT ACT CCA CCT ACG GCA AGT TCC TT 3' |
|---|---|
| J1C200-7 | 5' CTTGAATTC GTG GCA TCC GTG GAG TGG CAC TCG TC 3' |

The primers used in this experiment contain sequences identical to either HCV1 or J1. However, for cloning ease non HCV-1 sequences are sometimes included in particular primers. Primer J1C200-1, consisting of 17 nucleotides, is a sense primer whose sequence, 5' to 3', is identical to nucleotides 3794 to 3810 of HCV1. Primer J1C200-3, consisting of 20 nucleotides, is an anti-sense primer whose sequence, 5' to 3', is identical to the reverse complement of nucleotides 38 to 57 shown in FIG. 4. Primer J1C200-2, consisting of 36 nucleotides, is a sense primer whose sequence, 5' to 3', begins with CTTGAATTC and contines with sequence identical to nucleotides 3876 to 3903 of HCV1. Primer J1C200-4, consisting of 36 nucleotides, is an anti-sense

IV.E.

As described above, two rounds of PCR were performed on J1 cDNA to clone the J1 DNA sequences. homologous to nucleotides 5402 to 6121 of HCV1. The first round of PCR, PCRI, was performed using primers 511/16A and J1rc52, described below, to clone J1 DNA sequences homologous to nucleotides 4696 to 6151 of HCV1. Half of PCRI products were used as the template for a second round of PCR, PCRII, where primers 511/35A, described supra, and J1rc51, described below, were used.

The primers used in this experiment contain sequences identical to HCV1. However, for cloning ease or to anticipate J1 variability non HCV-1 sequences are sometimes included in particular primers. Primer 511/16A, consisting of 16 nucleotides, is a sense primer whose sequence, 5' to 3', begins with A and continues with sequence identical to nucleotides 4681 to 4695 of HCV1. Primer J1rc52, consisting of 31 nucleotides, is an anti-sense primer whose sequence, 5' to 3', begins with CTTAGAATTC, continues with sequence identical to the reverse complement of nucleotides 6152 to 6163 of HCV1, then contains a ATA and the last six nucleotides are identical to the reverse complement of nucleotides 6167 to 6172 of HCV1. Primer J1rc51, consisting of 34 nucleotides, is an anti-sense primer whose sequence, begins with CTTAGAATTC and continues with a sequence identical to the reverse complement of nucleotides 6122 to 6145 of HCV1.

The sequences of the above-mentioned primers are shown below:

J1rc52    5' CTTAGAATTC GAG GCT GCT GAG ATA GGC AGT 3'

511/16A   5' AAC AGG CTG CGT GGT C 3'

511/35A
  5' CTTGAATTC TCG TCT TGT CCG GGA AGC CGG CAA TC 3'

J1rc51
  5' CTTAGAATTC GGC AGC TGC ATC GCT CTC CGG CAC 3'

The final PCR products were run on an agarose gel and electroeluted. The isolated fragment was cut with EcoRI. The ends of the fragment were blunted using Klenow and then the fragment was cut with RsaI. This fragment was cloned into a bacterial vector and then subcloned into M13. Three clones were sequenced and the complete sequences are shown in FIG. 19. Partial sequence is shown in FIG. 16.

V

An HCV cDNA library containing sequences of the putative "NS1" region of the J1 isolate was created by directional cloning in λ-gt22. The library contains J1 DNA sequences that are homologous to nucleotide 239 to 2741 of HCV1. The cloning was accomplished using essentially the method described by Han and Rutter in GENETIC ENGINEERING, Vol 10 (J. K. Setlow, Ed., Plenum Publishing Co., 1988), except that the primers for the synthesis of the J1 cDNA were JHC67 and JHC68, described below, and the source of RNA was the J1 plasma. The RNA was extracted by low temperature guanidium thiocyanate method. The RNA is then converted to full length cDNA, which is cloned in a defined orientation relative to the lacZ promoter in λ-phage. Using this method, the HCV cDNAs to J1 RNA were inserted into the NotI site of λ-gt22. The presence of "NS1" sequences in the library was detected using as probe, Alx54.

Primer JHC68, consisting of 29 nucleotides, is a sense primer whose sequence, 5' to 3', begins with CGTGCGGCCGC, continues with sequence identical to nucleotides 221 to 236 of HCV-1 and ends with GT. Primer JHC67, consisting of 28 nucleotides, is an anti-sense primer whose sequence, 5' to 3', begins with GACGCGGCCGC and continues with sequence identical to the reverse complement of nucleotides 2742 to 2758 of HCV-1.

The DNA sequence was determined using the assymetric sequencing technique described inn Example IV.D., but substituting as primers for PCR amplification, Alx61 and Alx62, described below. The resulting sequence is shown in FIG. 17.

Primer ALX62, consisting of 30 nucleotides, is a sense primer whose sequence, 5' to 3', is identical to nucleotides 1919 to 1948 of HCV-1. Primer ALX61, consisting of 30 nucleotides, is an anti-sense primer whose sequence, 5' to 3', is identical to the reverse complement of nucleotides 2311 to 2340 of HCV-1.

The sequences of the primers and probes used to obtain the HCV cDNA library in λ-gt22, and to sequence the portion of the "NS1" region were the following.

JHC 67   5' GACGC GGCCG CCTCC GTGTC CAGCG CGT 3'

JHC 68   5' CGTGC GGCCG CAAGA CTGCT AGCCG AGGT 3'

ALX 61   5' ACCTG CCACT GTGTA GTGGT CAGCA GTAAC 3'

ALX 62   5' ACGGA CGTCT TCGTC CTTAA CAATA CCAGG 3'

ALX 54   5' GAACT TTGCG ATCTG GAAGA CAGGG ACAGG 3'

A 400 bp fragment of J1 HCV cDNA derived from the sequenced region was cloned into a derivative pGEM3z vector and maintained in HB101; the HCV cDNA may be removed from the vector with SacI and XbaI. Host cells transformed with the vector (JH-400 bp) have been deposited with the ATCC.

A pooled cDNA library was created from the J1 serum; the pooled library spans the J1 genome and is identified as HCV-J1 λ gt22. The pooled cDNA library was created by pooling aliquots of 11 individual cDNA libraries, which had been prepared using the directional cloning technique described above, except that the libraries were created from primers which were designed to yield HCV cDNAs which spanned the genome. The primers were derived from the sequence of HCV1, and included JHC 67 and JHC 68. The HCV cDNAs were inserted into the NotI site of λ-gt22. The pooled cDNA library, HCV-J1 λ gt22, has been deposited with the ATCC.

VI

The region homologous to nucleotide 55 to 211 of HCV1 was sequenced in two rounds of asymmetric PCR; therefore no subcloning into a plasmid or vector was necessary. However, the product of the first round of asymmetric PCR was cloned into pGEM3z for deposit.

RNA was extracted from 100 μl of serum following treatment with proteinase K and sodium dodecylsulfate (SDS). The samples were extracted with phenol-chloroform, and the RNA precipitated with ethanol.

HCV cDNA from the J1 isolate was prepared by denaturing the precipitated RNA with 0.01M MeHgOH; after ten minutes at room temperature, 2-mercaptoethanol was added to sequester the mercury ions. Immediately, the mix for the first strand of cDNA synthesis was added, and incubation was continued for 1 hr at 37° C. The conditions for the synthesis of the anti-sense strand were the following: 50 mM Tris HCl, pH 8.3, 75 mM KCl, 3 mm MgCl$_2$, 10 mM dithiothreitol, 500 μM each deoxynucleotide triphosphate, 250 pmol specific antisense cDNA primer r25, 250 units MMLV reverse transcriptase. In order to synthesize the second strand (sense), the synthesis reaction components were added, and incubated for one hour at 14° C. The components for the second strand reaction were as follows: 14 mM Tris HCl, pH 8.3, 68 mM KCl, 7.5 mM ammonium sulfate, 3.5 mM MgCl$_2$, 2.8 mM dithiothreitol, 25 units DNA polymerase I, and one unit RNase H. The reactions were terminated by heating the samples to 95° C. for 10 minutes, followed by cooling on ice.

The HCV cDNA was amplified by two rounds of PCR. The first round was accomplished using 20 μl of the cDNA mix. The conditions for the PCR reaction were as follows: 10 mM Tris HCl, pH 8.3, 50 mM KCl, 1.5 mM MgCl$_2$, 0.002% gelatin, 200 mM each of the deoxynucleotide triphosphates, and 2.5 units Amplitaq. The PCR thermal cycle was as follows: 94° C. one minute, 50° C. one minute, 72° C. one minute, repeated 40 times followed by seven minutes at 72° C. The second round of PCR was accomplished using nested primers (i.e., primers which bound to an internal region of the first round of PCR amplified product) to increase the specificity of the PCR products. One percent of the first PCR reaction was amplified essentially as the first round, except that the primers were substituted, and the second step in the PCR reaction was at 60° C. instead of 50° C. The primers used for the first round of PCR were ALX90 and r14. The primers used for the second round of PCR were r14 and p14.

Primer ALX90, consisting of 28 nucleotides, is a sense primer whose sequence, 5' to 3', is identical to nucleotides 8 to 35 of HCV-1. Primer r25, consisting of 24 nucleotides, is an anti-sense primer whose sequence, 5' to 3', is identical to the reverse complement of nucleotides 661 to 684 of HCV-1. Primer p14, consisting of 24 nucleotides, is a sense primer whose sequence, 5' to 3', is identical to nucleotides 31 to 54 of HCV-1. Primer r14, consisting of 21 nucleotides, is an antisense primer whose sequence, 5' to 3', is almost identical to the reverse complement of nucleotides 626 to 646 of HCV-1 except position 4 of the primer instead of a G should be a C and at position 13 instead of a T should be an A.

From this PCR pool one aliquot was sequenced using r14 and p14 as primers in the below mentioned procedure. A second aliquot was used as the template for another round of PCR using R31 and P32 primers. This new round of PCR was done to obtain enough DNA to sequence the internal portion of the original 615 bp fragment. The new PCR product was sequenced using R31 and P32 as primers, described below, and the same below-mentioned protocol.

Primer P32, consisting of 23 nucleotides, is a sense primer whose sequence, 5' to 3', is identical to nucleotides 183 to 205 of HCV-1. Primer R31, consisting of 20 nucleotides, is an anti-sense primer whose sequence, 5' to 3', is almost identical to the reverse complement of nucleotides 512 to 531 of HCV-1 except that position 6 of the primer can be either A or G.

The PCR products were gel purified, the material which migrated as having about 615 bp was isolated, and sequenced by a modification of the Sanger dideoxy chain termination method, using $^{32}$P-ATP as label. In the modified sequencing method, the sequence replication was primed using the appropriate primers; the double stranded DNA was melted for 3 minutes at 95° C. and was quickly chilled on ice, and the synthesis of labeled dideoxy terminated polynucleotides was catalyzed by Bst polymerase (obtained from BioRad Corp.) at 65° C., according to the manufacturer's directions. The sequencing was performed using 500 ng to 1 μg of PCR product per sequencing reaction.

The sequences of the primers used in this example are shown below.

| | |
|---|---|
| r25 | 5' ACC TTA CCC AAA TTG CGC GAC CTA 3' |
| ALX90 | 5' CCA TGA ATC ACT CCC CTG TGA GGA ACT A 3' |
| r14 | 5' GGG CCC CAG CTA GGC CGA GA 3' |
| p14 | 5' AAC TAC TGT CTT CAC GCA GAA AGC 3' |
| P32 | 5' AAC CCG CTC AAT GCC TGG AGA TT 3' |
| R31 | 5' GGC CGX CGA GCC TTG GGG AT 3' | where X=A or G

The sequence of the region in the J1 isolate which encompasses the 5'-untranslated region as well as a part of the region of the putative "Core" is shown in FIG. 18. In the figure, amino acids encoded in the J1 sequence are shown above the nucleotide sequence. The sequence of the prototype HCV1 is shown below the J1 sequence; the dashes indicate sequence homology with J1. The differing amino acids encoded in the HCV1 sequence are shown below the HCV1 sequence.

An HCV cDNA fragment which is a representative of the 615 bp J1 sequence described above (TC 600bp) was cloned into a derivative pGEM3Z and maintained in host HB101; the HCV cDNA fragment may be removed with SacI and XbaI. This material is on deposit with the ATCC.

Patent Microorganism Depository-deposited under Budapest Treaty terms are listed below.

| Deposited Materials | Accession Number | Deposit Date |
|---|---|---|
| *E. coli* DH5/pS1-8791a | BP-2593 | 9/15/1989 |
| (This clone contains 427 bp of the HS5 domain of J1) | | |
| *E. coli* HB101/pU1-1216c | BP-2594 | 9/15/1989 |
| (This clone contains 351 bp of the E/NS1 domains of J1) | | |
| *E. coli* HB101/pU1-4652d | BP-2595 | 9/15/1989 |
| (This clone contains 583 bp of the NS3 domain of J1) | | |
| *E. coli* DH5α/pS1-713c | BP-2637 | 11/1/1989 |
| (This clone dontains 580 bp of the E domain of J1) | | |
| *E. coli* DH5α/pS7-28c | BP-2638 | 11/1/1989 |
| (This clone contains 552 bp of the C/E domain of J7) | | |
| *E. coli* DH5α/ps1-1519 | BP3081 | 8/30/90 |

The following vectors described in the Examples were deposited with the American Type Culture Collection (ATCC), 12301 Parklawn Dr., Rockville, Md. 20852, and have been assigned the following Accession Numbers. The deposits were made under the terms of the Budapest Treaty.

| Deposited Materials | Accession Number | Deposit Date |
|---|---|---|
| TC-600BP (in *E. coli* HB101/pGEM3Z) | 68393 | 9/11/90 |
| JH-400bp (in *E. coli* HB101/PGEM3Z) | 68394 | 9/11/90 |
| AW-300bp (in *E. coli* HB101/PGEM3Z) | 68392 | 9/11/90 |
| AW-770bp-N (in *E. coli* HB101/pM1E) | 68395 | 9/11/90 |
| AW-700bp-C (in *E. coli* DH5α-F'/M13mp10) | 40888 | 9/11/90 |
| J1 5-1-1 (in *E. coli* DH5α-F'/M13mp10) | 40887 | 9/11/90 |
| HCV-J1 λ gt22 | 40884 | 9/6/90 |

These deposits are provided for the convenience of those skilled in the art. These deposits are neither an admission that such deposits are required to practice the present invention nor that equivalent embodiments are not within the skill of the art in view of the present disclosure. The public availability of these deposits is not a grant of a license to make, use or sell the deposited materials under this or any other patent. The nucleic acid sequences of the deposited materials are incorporated in to present disclosure by reference, and are controlling if in conflict with any sequences described herein.

While the present invention has been described by way specific examples for the benefit of those in the field, the scope of the invention is not limited as additional embodiments will be apparent to those of skill in the art from the present disclosure.

We claim:

1. An isolated hepatitis C virus polypeptide comprising an antigen comprising a sequence as shown in FIG. 6, FIG. 7, FIG. 8, FIG. 9, FIG. 10, or encoded by a polynucleotide sequence deposited under Accession Numbers BP-2593, BP-2594, BP-2595, BP-2637, or BP-2638, said encoded sequence being in frame with the corresponding amino acid sequences set out in FIG. 6, FIG. 7, FIG. 8, FIG. 9, or FIG. 10, or a fragment thereof, wherein said antigen is not immunologically cross-reactive with HCV-1.

2. The polypeptide according to claim 1 wherein said antigen or fragment thereof is shown in FIG. 6.

3. The polypeptide according to claim 1 wherein said antigen or fragment thereof is shown in FIG. 7.

4. The polypeptide according to claim 1 wherein said antigen or fragment thereof is shown in FIG. 8.

5. The polypeptide according to claim 1 wherein said antigen or fragment thereof is shown in FIG. 9.

6. The polypeptide according to claim 1 wherein said antigen or fragment thereof is shown in FIG. 10.

7. The polypeptide according to claim 1 wherein said antigen or fragment thereof is encoded by a polynucleotide sequence deposited under Accession Number BP-2593.

8. The polypeptide according to claim 7 wherein said antigen or fragment thereof is encoded by a polynucleotide sequence deposited under Accession Number BP-2594.

9. The polypeptide according to claim 7 wherein said antigen or fragment thereof is encoded by a polynucleotide sequence deposited under Accession Number BP-2595.

10. The polypeptide according to claim 7 wherein said antigen or fragment thereof is encoded by a polynucleotide sequence deposited under Accession Number BP-2637.

11. The polypeptide according to claim 7 wherein said antigen or fragment thereof is encoded by a polynucleotide sequence deposited under Accession Number BP-2638.

12. A polypeptide according to claim 1 immobilized on a solid support.

13. A polypeptide according to either of claims 1 or 12 wherein said antigen or fragment thereof is at least 10 amino acids.

14. A polypeptide according to either of claims 1 or 12 wherein said antigen or fragment thereof is at least 15 amino acids.

* * * * *